(12) United States Patent
Bachhav et al.

(10) Patent No.: US 11,021,474 B2
(45) Date of Patent: Jun. 1, 2021

(54) N-[5-(AMINOSULFONYL)-4-METHYL-1,3-THIAZOL-2-YL]-N-METHYL-2-[4-(2-PYRIDINYL)-PHENYL]-ACETAMIDE FREE BASE HEMIHYDRATE, METHODS OF MANUFACTURE AND USES THEREOF

(71) Applicant: AiCuris Anti-Infective Cures GmbH, Wuppertal (DE)

(72) Inventors: Yogeshwar Bachhav, Mumbai (IN); Wilfried Schwab, Werder (DE); Alexander Birkmann, Wuppertal (DE); Kurt Voegtli, Oberhofen AG (CH)

(73) Assignee: AiCuris Anti-Infective Cures GmbH, Wuppertal (DE)

( * ) Notice: Subject to any disclaimer, the term of this patent is extended or adjusted under 35 U.S.C. 154(b) by 0 days.

(21) Appl. No.: 16/464,448

(22) PCT Filed: Nov. 28, 2017

(86) PCT No.: PCT/EP2017/080653
§ 371 (c)(1),
(2) Date: May 28, 2019

(87) PCT Pub. No.: WO2018/096170
PCT Pub. Date: May 31, 2018

(65) Prior Publication Data
US 2020/0123145 A1   Apr. 23, 2020

(30) Foreign Application Priority Data

Nov. 28, 2016   (EP) ..................... 16200967

(51) Int. Cl.
| | | |
|---|---|---|
| *A61K 31/427* | (2006.01) | |
| *A61K 31/4439* | (2006.01) | |
| *C07D 417/12* | (2006.01) | |
| *C07D 417/10* | (2006.01) | |
| *A61P 31/22* | (2006.01) | |

(52) U.S. Cl.
CPC .................. *C07D 417/12* (2013.01)

(58) Field of Classification Search
CPC .............. A61K 31/427; A61K 31/4439; C07D 417/12; C07D 417/10; A61P 31/22

USPC ................ 514/342, 371, 369; 548/185, 194; 546/270.7

See application file for complete search history.

(56) References Cited

U.S. PATENT DOCUMENTS

| | | |
|---|---|---|
| 7,105,553 B2 | 9/2006 | Fischer et al. |
| 8,784,887 B2 | 7/2014 | Laich et al. |
| 9,119,786 B2 | 9/2015 | Schwab et al. |
| 9,592,225 B2 | 3/2017 | Schwab et al. |
| 9,889,124 B2 | 2/2018 | Schwab et al. |
| 10,137,117 B2 | 11/2018 | Schwab et al. |
| 2004/0006076 A1 | 1/2004 | Fischer et al. |
| 2008/0220059 A1 | 9/2008 | Laich et al. |
| 2014/0065224 A1 | 3/2014 | Schwab et al. |
| 2015/0366849 A1 | 12/2015 | Schwab et al. |
| 2016/0008341 A1 | 1/2016 | Schwab et al. |
| 2017/0348297 A1 | 12/2017 | Schwab et al. |

FOREIGN PATENT DOCUMENTS

| | | | | |
|---|---|---|---|---|
| CA | 2396720 A1 | * | 7/2001 | .............. A61P 11/00 |
| CA | 2602750 A1 | * | 10/2006 | ........... C07D 417/12 |
| WO | 01/47904 A1 | | 7/2001 | |
| WO | 2006/103011 A1 | | 10/2006 | |
| WO | 2013/045491 A1 | | 4/2013 | |

OTHER PUBLICATIONS

International Search Report dated Jan. 23, 2018 issued in corresponding PCT/EP2017/080653 application (3 pages).

* cited by examiner

*Primary Examiner* — Joseph R Kosack
*Assistant Examiner* — Sagar Patel
(74) *Attorney, Agent, or Firm* — Millen White Zelano and Branigan, PC; John Sopp

(57) ABSTRACT

The present invention relates to the field of anti-viral active agents, particularly the free base hemihydrate form of N-[5-(aminosulfonyl)-4-methyl-1,3-thiazol-2-yl]-N-methyl-2-[4-(2-pyridinyl)-phenyl]-acetamide as well as methods for the manufacture thereof. The present invention relates also to the use of the above compound in the treatment of human herpes virus infections and in the preparation of pharmaceuticals comprising said compound.

11 Claims, 10 Drawing Sheets

Figure 3:
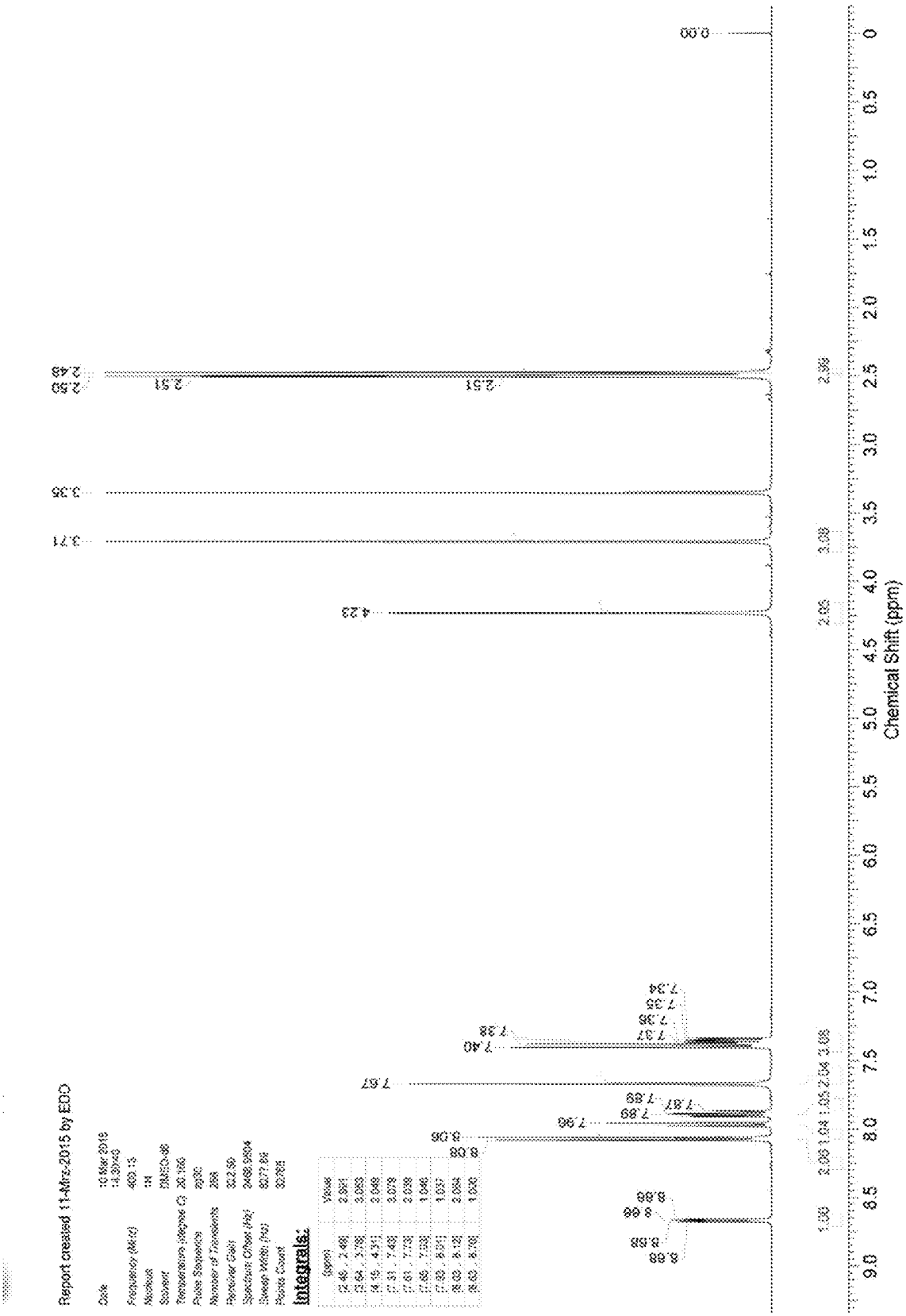

Fig. 3: $^1$H-NMR spectrum

Figure 4:
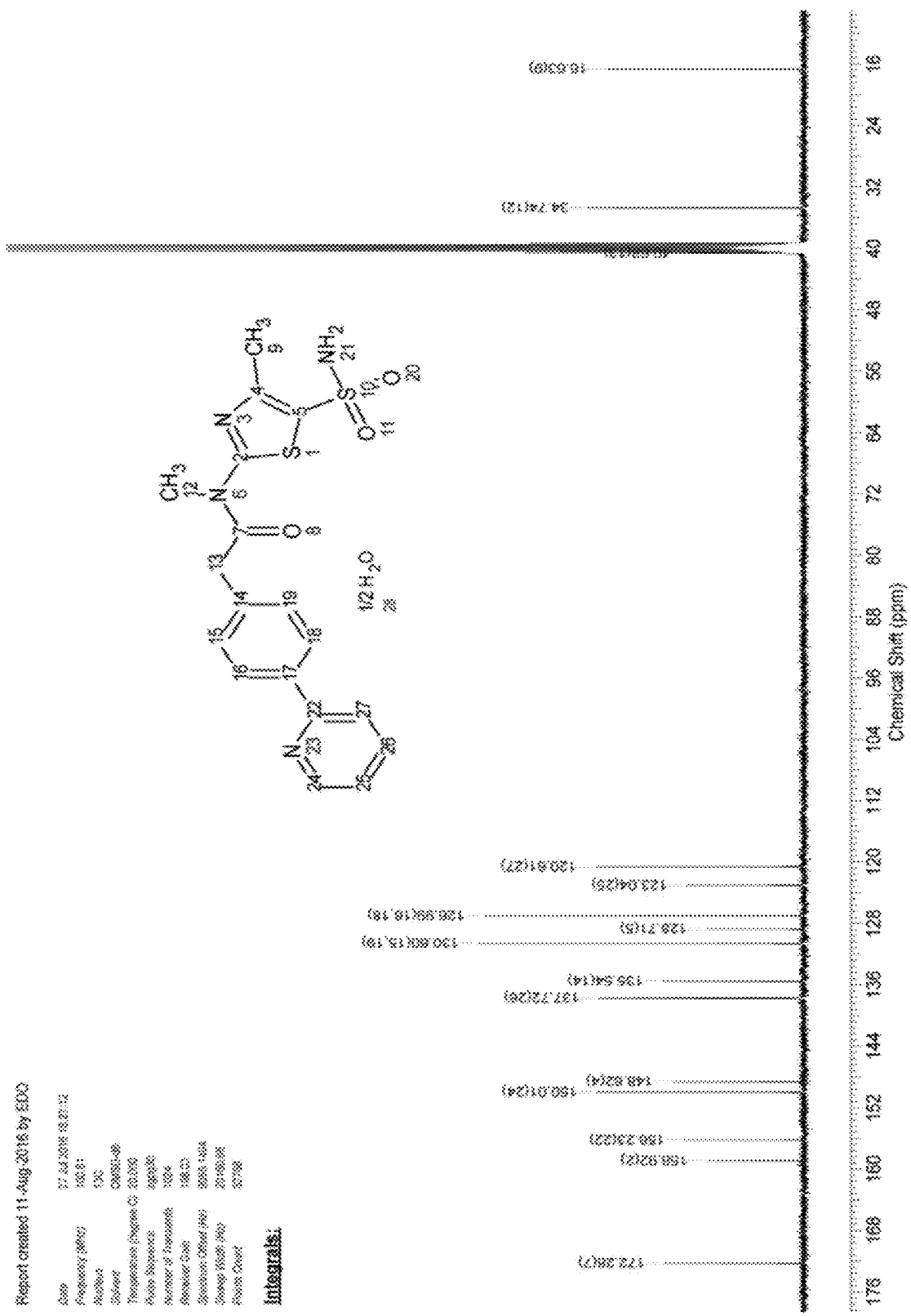

Fig. 4 - $^{13}$C-NMR Spectrum

Figure 5:
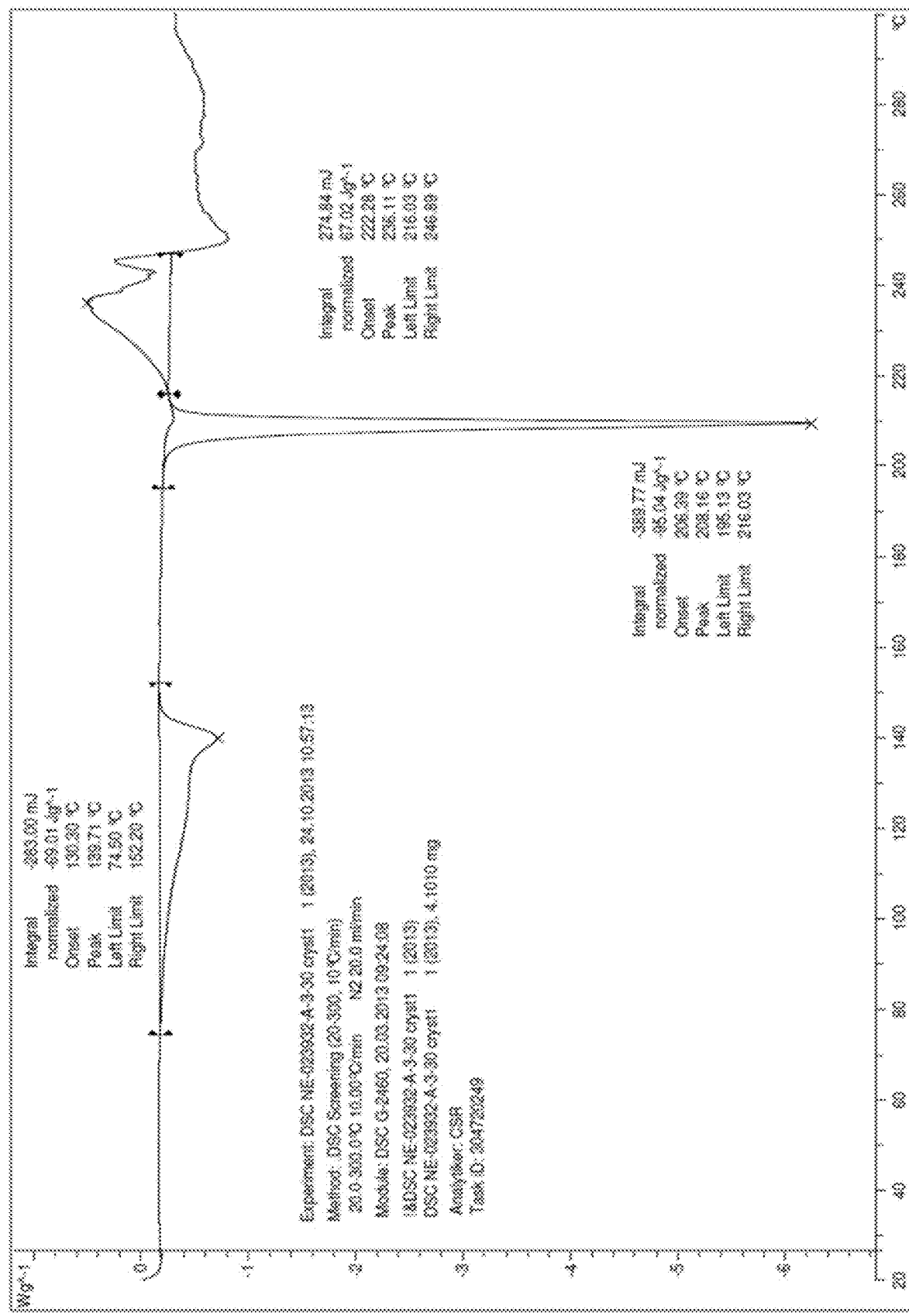

Fig. 5 – DSC (melting point method)

Figure 7:
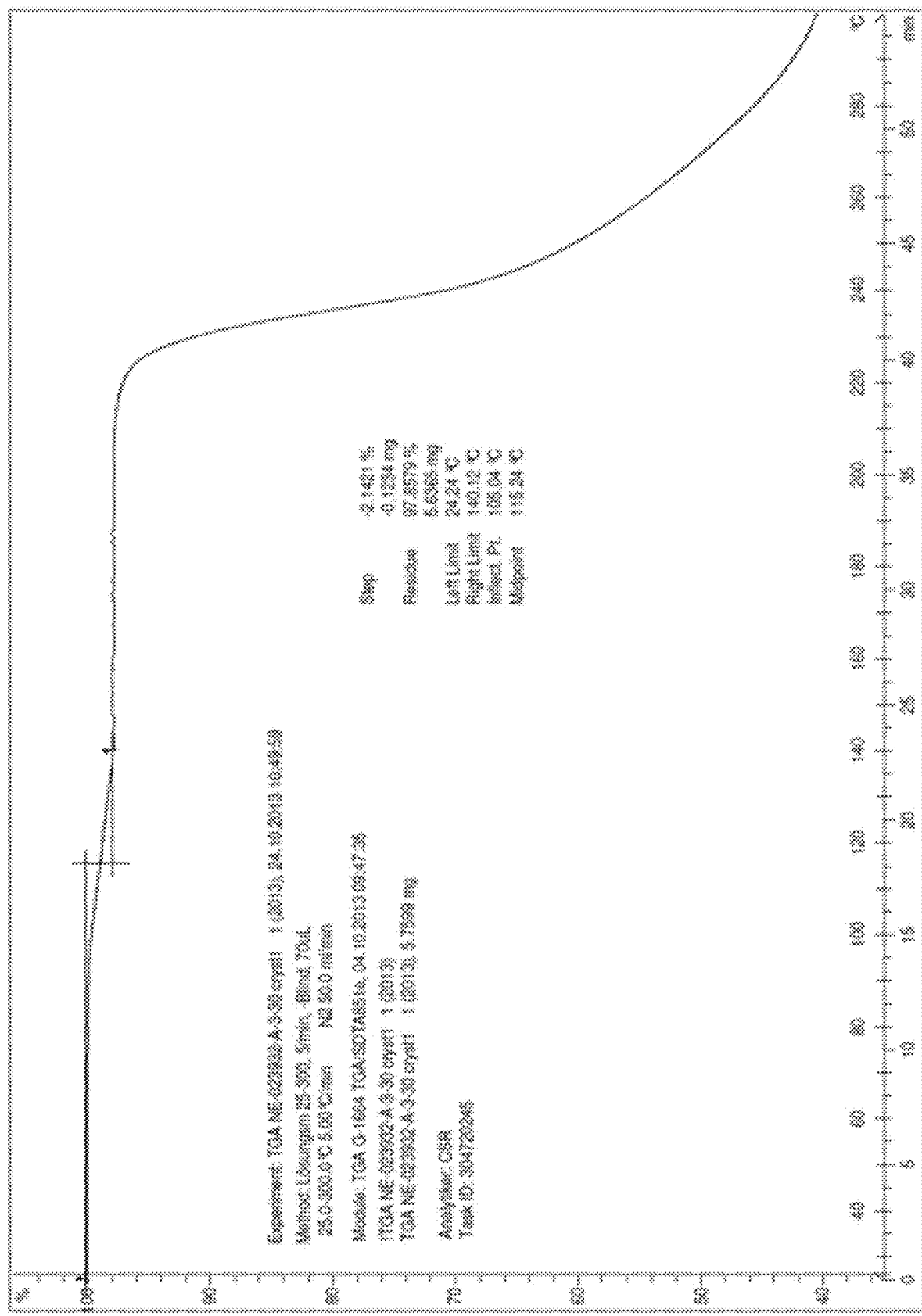

Fig. 7 – TGA analysis

Fig. 8
A) Ortep Plot (50%) of the structure corresponding to Form C – View A
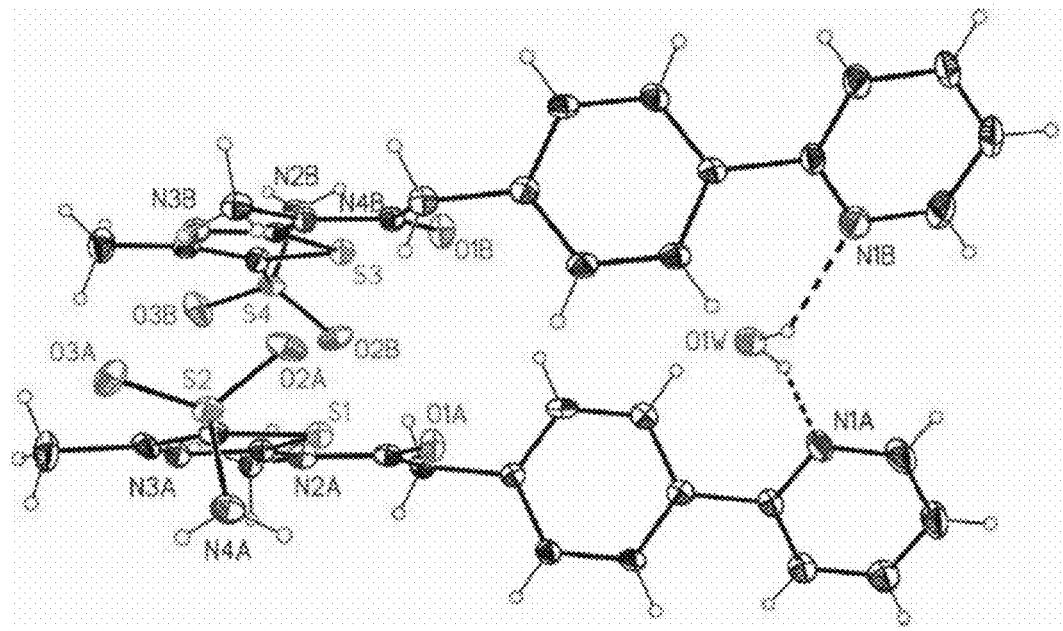
B) Ortep Plot (50%) of the structure corresponding to Form C – View B
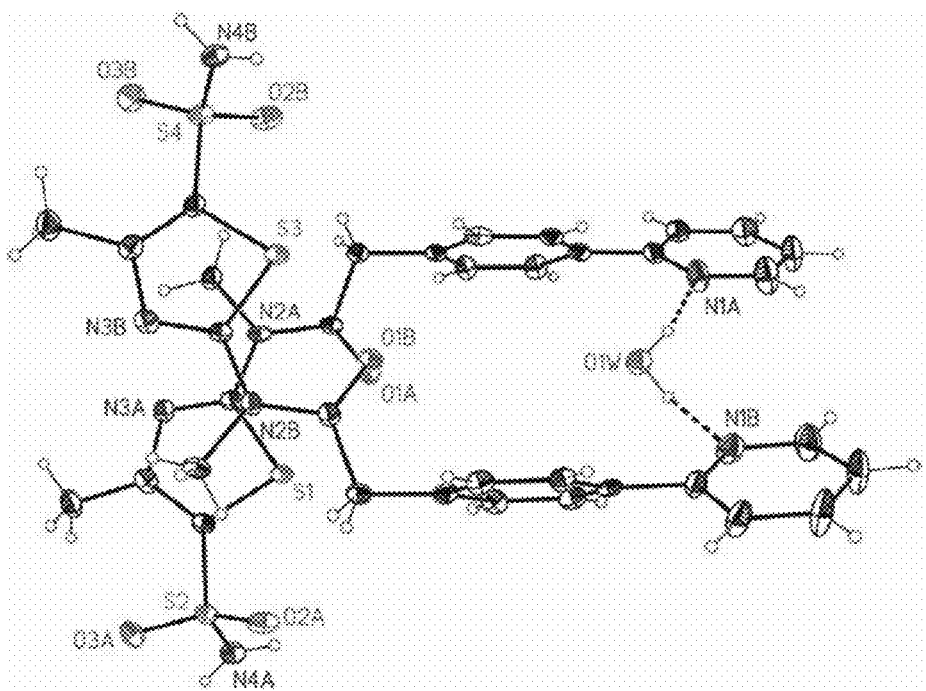

Fig. 9. IR spectrum
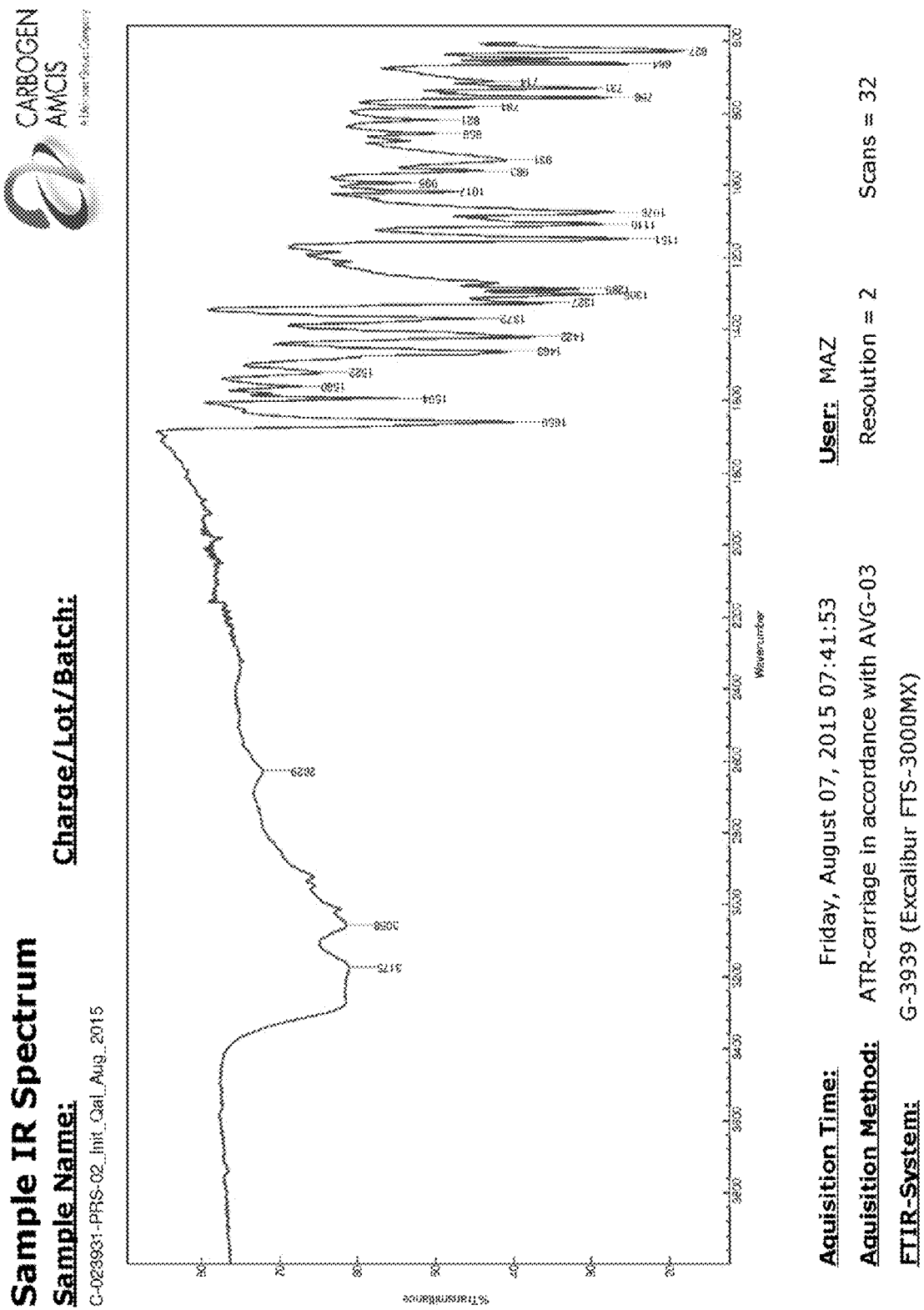

N-[5-(AMINOSULFONYL)-4-METHYL-1,3-THIAZOL-2-YL]-N-METHYL-2-[4-(2-PYRIDINYL)-PHENYL]-ACETAMIDE FREE BASE HEMIHYDRATE, METHODS OF MANUFACTURE AND USES THEREOF

FIELD OF THE INVENTION

The present invention relates to the field of anti-viral active agents, particularly the free base hemihydrate form of N-[5-(aminosulfonyl)-4-methyl-1,3-thiazol-2-yl]-N-methyl-2-[4-(2-pyridinyl)-phenyl]-acetamide (in the following also referred to as "Pritelivir" and/or "free base hemihydrate") as well as methods for the manufacture thereof. The present invention relates also to the use of the above compound in the treatment of human herpes virus infections and in the preparation of pharmaceuticals comprising said compound.

BACKGROUND

N-[5-(aminosulfonyl)-4-methyl-1,3-thiazol-2-yl]-N-methyl-2-[4-(2-pyridinyl)-phenyl]-acetamide is a known anti-viral compound used in the treatment of herpes simplex viruses (Herpes Simplex Virus 1 and 2, respectively) as disclosed in WO2006103011A1. HSV-1 and/or 2 infections are the cause of diseases such as labial herpes (cold sores mainly due to infections with HSV-1), genital herpes (mainly due to HSV-2 infections), but may rarely also cause severe diseases, such as keratitis and encephalitis. The viruses are ubiquitously distributed throughout the world. A well-known drug used in the treatment of herpes simplex infections is acyclovir (2-Amino-1,9-dihydro-9-((2-hydroxyethoxy)methyl)-6H-purin-6-one), which is a specific inhibitor of the viral DNA polymerase.

Antiviral drugs against herpes viruses can be administered to a patient in multiple ways, e.g., systemically, topically, and parenterally. As with all drugs, the stability upon storage and when used on or in the patients is of utmost importance. While the stability of the N-[5-(aminosulfonyl)-4-methyl-1,3-thiazol-2-yl]-N-methyl-2-[4-(2-pyridinyl)-phenyl]-acetamide is already good, it is an object to provide even more stable, for example, more storage stable and photostable compounds that provide for pharmaceutical compositions having a very high degree of purity.

The stability of the inventive compound ensures that pharmaceutical compositions that are formulated to comprise the N-[5-(aminosulfonyl)-4-methyl-1,3-thiazol-2-yl]-N-methyl-2-[4-(2-pyridinyl)-phenyl]-acetamide free base hemihydrate have a substantially reduced amount of decomposition/degradation products. In other words, the active ingredient is present at higher purity (i.e. lower amount of degradation products) or the dose of active compound per volume unit is higher. This characteristic permits reducing the initial amount of active N-[5-(aminosulfonyl)-4-methyl-1,3-thiazol-2-yl]-N-methyl-2-[4-(2-pyridinyl)-phenyl]-acetamide upon formulation of pharmaceutical compositions, because the effective concentration per volume unit of a given pharmaceutical is achieved at respective lower amount and can be maintained for a longer period of time compared with formulations that are not based on the hemihydrate form of N-[5-(aminosulfonyl)-4-methyl-1,3-thiazol-2-yl]-N-methyl-2-[4-(2-pyridinyl)-phenyl]-acetamide.

Further, the herein described inventive manufacturing process of the N-[5-(aminosulfonyl)-4-methyl-1,3-thiazol-2-yl]-N-methyl-2-[4-(2-pyridinyl)-phenyl]-acetamide free base hemihydrate ensures that impurities arising from the production process, e.g. from solvents, or degradation products of either the active compound or other compounds used in the manufacturing process are essentially absent or not detectable by analytical methods. By contrast, it is known that mesylate salts of active compounds are an example of an essentially stable form, but they contain potentially harmful impurities arising in conventionally produced compounds bearing, e.g., the potential risk of genotoxic impurities or degradants formed during the manufacturing process or formed during storage.

Therefore, the present invention provides unexpectedly stable forms of N-[5-(aminosulfonyl)-4-methyl-1,3-thiazol-2-yl]-N-methyl-2-[4-(2-pyridinyl)-phenyl]-acetamide in form of the free base hemihydrate that per se have a high degree of purity after manufacturing and due to the stability can be stored for prolonged periods of time. Further, upon formulation as pharmaceuticals and storage the active ingredient N-[5-(aminosulfonyl)-4-methyl-1,3-thiazol-2-yl]-N-methyl-2-[4-(2-pyridinyl)-phenyl]-acetamide is present at high concentrations essentially without or extremely low decomposition which ensures that the therapeutically effective concentration per volume unit of a pharmaceutical remains high without any significant decreasing of active substance content due to degradation processes.

SHORT DESCRIPTION OF THE FIGURES

Figure 1:
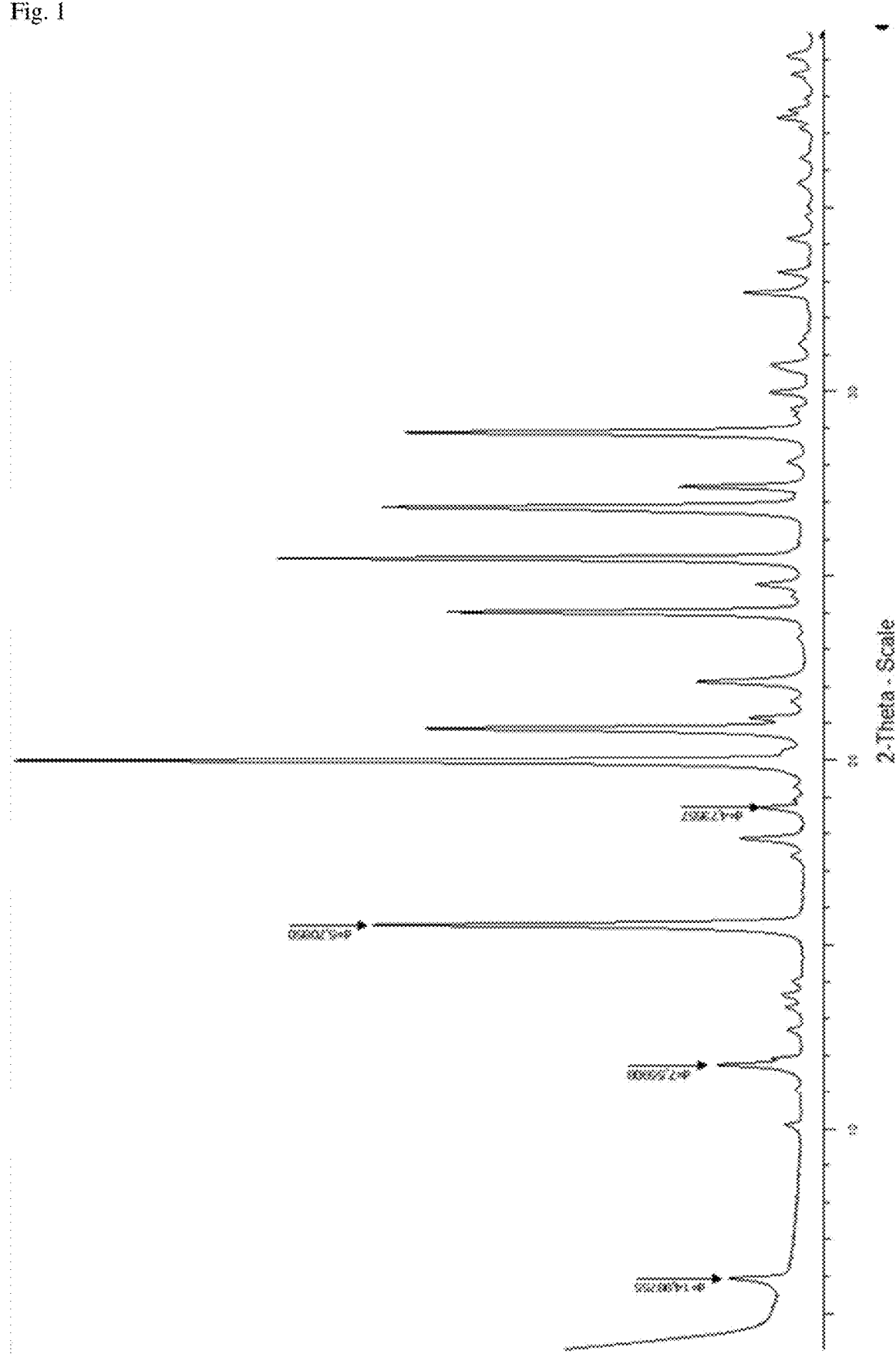

FIG. 1: X-Ray powder diffraction (XRPD) analysis of N-[5-(aminosulfonyl)-4-methyl-1,3-thiazol-2-yl]-N-methyl-2-[4-(2-pyridinyl)-phenyl]-acetamide free base hemihydrate FIG. 2: Microscope pictures show that N-[5-(aminosulfonyl)-4-methyl-1,3-thiazol-2-yl]-N-methyl-2-[4-(2-pyridinyl)-phenyl]-acetamide free base hemihydrate consists of rod-like crystals showing birefringence under the microscopy FIG. 3: $^1$H-NMR spectrum of N-[5-(aminosulfonyl)-4-methyl-1,3-thiazol-2-yl]-N-methyl-2-[4-(2-pyridinyl)-phenyl]-acetamide free base hemihydrate FIG. 4: $^{13}$C-NMR spectrum of N-[5-(aminosulfonyl)-4-methyl-1,3-thiazol-2-yl]-N-methyl-2-[4-(2-pyridinyl)-phenyl]-acetamide free base hemihydrate FIG. 5—DSC of N-[5-(aminosulfonyl)-4-methyl-1,3-thiazol-2-yl]-N-methyl-2-[4-(2-pyridinyl)-phenyl]-acetamide free base hemihydrate.

Figure 6:
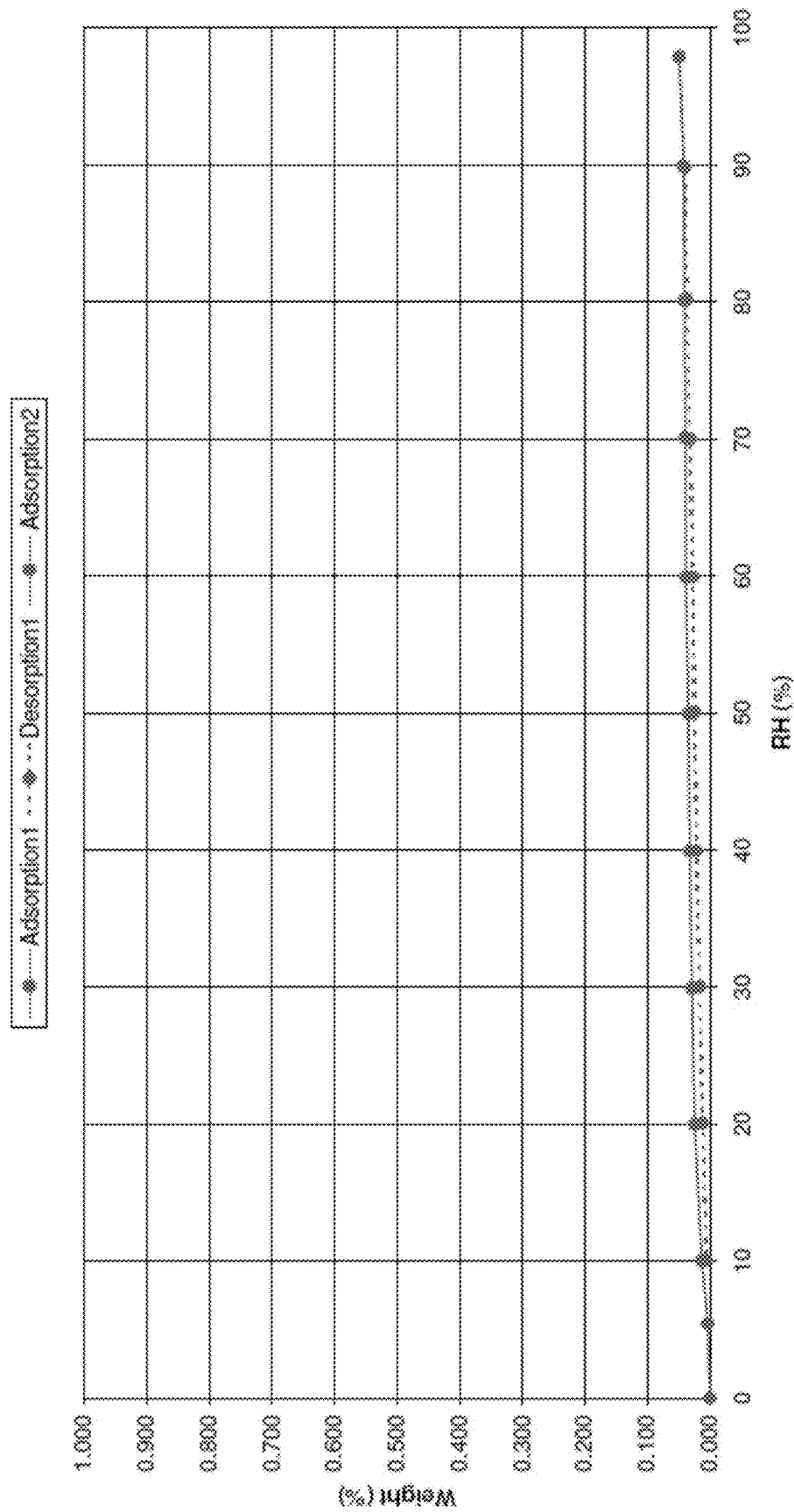
Figure 6:
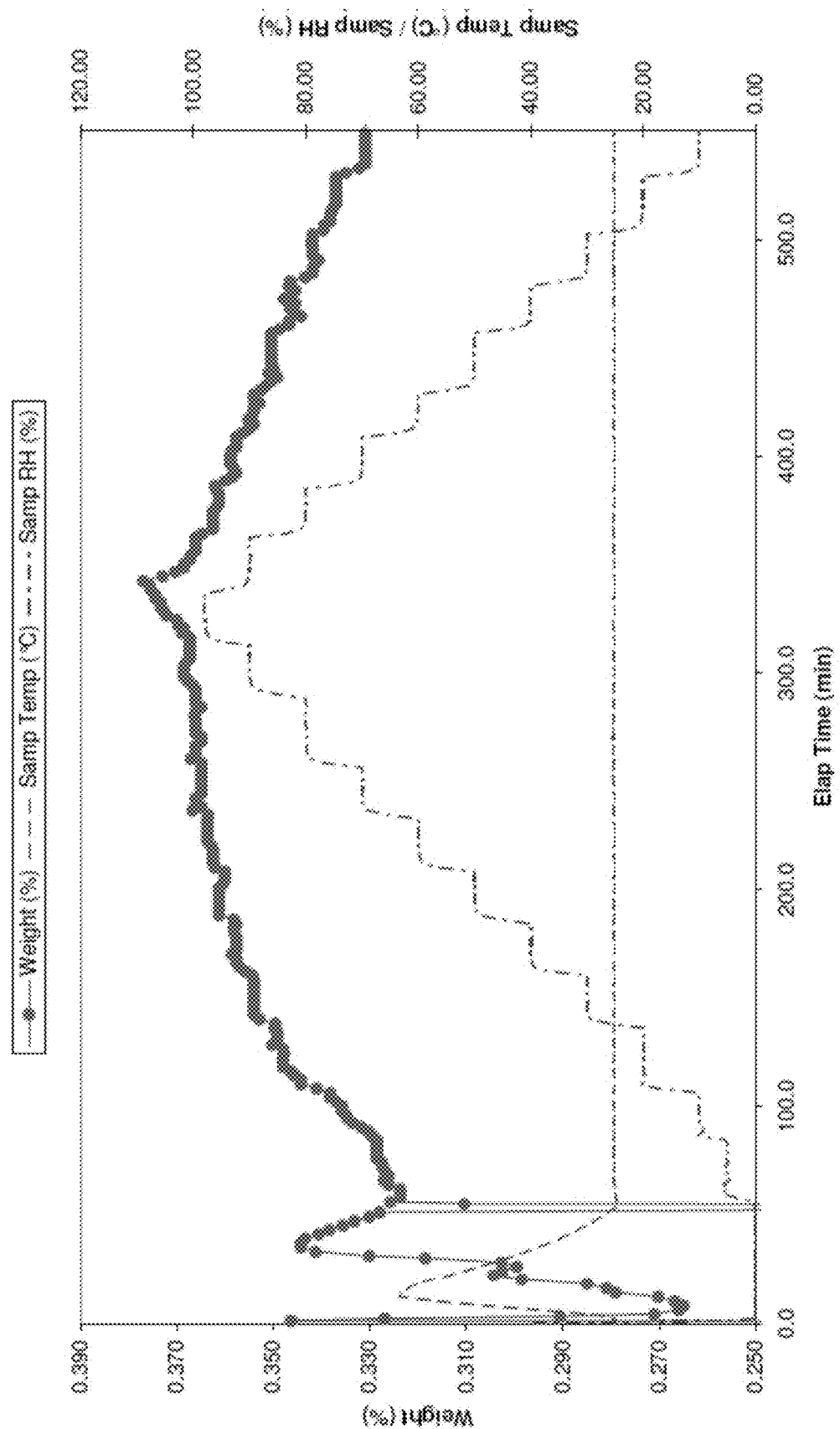

FIG. 6—DVS cycle of N-[5-(aminosulfonyl)-4-methyl-1,3-thiazol-2-yl]-N-methyl-2-[4-(2-pyridinyl)-phenyl]-acetamide free base hemihydrate shows that there is no significant weight loss/increase and indicates that form C is a stable hemihydrate. A): weight vs. relative humidity, B): measurement over time.

FIG. 7—TGA of N-[5-(aminosulfonyl)-4-methyl-1,3-thiazol-2-yl]-N-methyl-2-[4-(2-pyridinyl)-phenyl]-acetamide free base hemihydrate indicates solvent loss. The 2.1% by weight correspond to the hemihydrate form.

FIGS. 8A) and B) shows an Ortep Plot of Form C of N-[5-(aminosulfonyl)-4-methyl-1,3-thiazol-2-yl]-N-methyl-2-[4-(2-pyridinyl)-phenyl]-acetamide free base hemihydrate from different angles FIG. 9—Infrared spectroscopic data of N-[5-(aminosulfonyl)-4-methyl-1,3-thiazol-2-yl]-N-methyl-2-[4-(2-pyridinyl)-phenyl]-acetamide free base hemihydrate

DETAILED DESCRIPTION OF THE INVENTION

Before describing the invention in detail, it is deemed expedient to provide definitions for certain technical terms used throughout the description. Although the present invention will be described with respect to particular embodiments, this description is not to be construed in a limiting sense. Before describing in detail exemplary embodiments of the present invention, definitions important for understanding the present invention are given.

Definitions

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

According to the present invention, the term "antiviral effective amount" means the total amount of each active component that is sufficient to show a meaningful patient benefit, i.e., healing of acute conditions characterized by inhibition of the herpes virus infection. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat, treating, treatment" as used herein and in the claims means preventing or ameliorating diseases associated with herpes virus infection. The terms "prophylaxis or prevention" as used herein and in the claims refers to the administration or use of the herein disclosed compounds or compositions in order to protect a non-infected organism or a non-infected cell of an organism from being infected, i.e., an organism may be infected by a virus, but the spread of the virus in the organism (from cell to cell) or within the organisms' social environment is prevented. The organism may be human or other mammal. In one aspect of the invention, the organism to whom the compound or pharmaceutical composition is administered is a human being that is infected by a herpes virus, e.g., HSV-1 and/or HSV-2, or a human being that is in danger of being infected by such viruses.

The physical characterization of the free base hemihydrate referred to herein was performed using compendial methods as per European Pharmacopoeia (Ph. Eur.) and/or the U.S. Pharmacopeial Convention (USP).

Herein below, various embodiments of the invention are explained in more detail. Wherever, respective alternatives in terms of ingredients in compositions, types of pharmaceutical compositions, concentrations of ingredients, periods of time of administration, frequencies of administration, medical indications to be treated are mentioned, the person skilled in the would immediately understand that individual combinations can be made as long as these are technically possible or if not otherwise explicitly indicated.

In one embodiment the present application relates to N-[5-(amino-sulfonyl)-4-methyl-1,3-thiazol-2-yl]-N-methyl-2-[4-(2-pyridinyl)phenyl]acetamide free base hemihydrate having the molecular formula $C_{18}H_{18}N_4O_3S_2 \times 0.5H_2O$. An Ortep Plot of the compound is shown in FIGS. 8A and B.

The free base hemihydrate comprises two molecules of Formula (I):

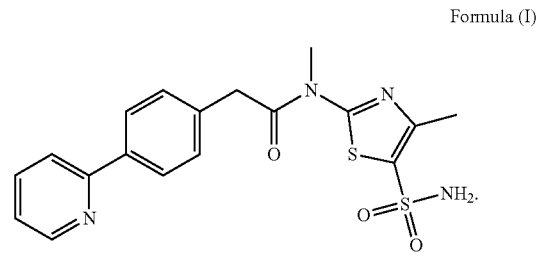 [SMILES: Cc1nc(N(C)C(=O)Cc2ccc(-c3ccccn3)cc2)sc1S(N)(=O)=O]

Formula (I)

These two molecules of Formula (I) are bound to each other by one water molecule which is surprisingly located between two aromatic rings respectively found at the end of the compounds. This surprising conformation provides the hemihydrate with an unusually high stability that was not found in any other polymorphs, salts, polymorphs of salts and solvates/hydrates identified in a polymorph screening on the monohydrate form of the above compound according to Formula (I) as described in the examples section. In one embodiment, solids comprising or consisting of the hemihydrate are highly storage stable and also show a surprising photostability.

As used herein, the terms "storage stable" or "photostable" and corresponding terms indicate that the hemihydrate does not decompose or degrade for prolonged periods of time. This means that the N-[5-(amino-sulfonyl)-4-methyl-1,3-thiazol-2-yl]-N-methyl-2-[4-(2-pyridinyl)phenyl]acetamide free base hemihydrate concentration remains constantly very high as can be measured using a standard measuring method permitting the identification of said compound and/or decomposition products thereof, e.g. HPLC, XRPD, and $^{13}C$— and $^{1}H$-NMR-spectroscopy methods showing the standard profile of N-[5-(amino-sulfonyl)-4-methyl-1,3-thiazol-2-yl]-N-methyl-2-[4-(2-pyridinyl)phenyl]acetamide. As mentioned above, the physical characterization of the free base hemihydrate referred to herein was performed using compendial methods as per European Pharmacopoeia (Ph. Eur.) and/or the U.S. Pharmacopeial Convention (USP).

Due to the general absence of impurities (either from the manufacturing process or due to decomposition of N-[5-(amino-sulfonyl)-4-methyl-1,3-thiazol-2-yl]-N-methyl-2-[4-(2-pyridinyl)phenyl]acetamide free base or the N-[5-(amino-sulfonyl)-4-methyl-1,3-thiazol-2-yl]-N-methyl-2-[4-(2-pyridinyl)phenyl]acetamide hemihydrate, the purity of N-[5-(amino-sulfonyl)-4-methyl-1,3-thiazol-2-yl]-N-methyl-2-[4-(2-pyridinyl)phenyl]acetamide in the manufacturing product and in upon formulation of compositions or medicaments comprising initially the N-[5-(amino-sulfonyl)-4-methyl-1,3-thiazol-2-yl]-N-methyl-2-[4-(2-pyridinyl)phenyl]acetamide free base hemihydrate is very high, i.e. a high concentration of N-[5-(amino-sulfonyl)-4-methyl-1,3-thiazol-2-yl]-N-methyl-2-[4-(2-pyridinyl)phenyl]acetamide per volume unit is achieved. This is very beneficial when the compound of the invention is used in the formulation of pharmaceuticals and medicaments, because the effective concentration of the active compound per volume unit is very high. This allows reducing the amount of the inventive N-[5-(amino-sulfonyl)-4-methyl-1,3-thiazol-2-yl]-N-methyl-2-[4-(2-pyridinyl)phenyl]acetamide free base hemihydrate upon formulation whilst at the same time keeping a suitably high effective dose of the active compound. This is particularly desirable for pharmaceuticals used as topical compositions (unlike single unit dosage forms, e.g. essentially solid pharmaceuticals in form of tablets, etc., or—as another example—dosage forms for reconstitution in a pharmaceutically acceptable medium or carrier for immediate use as understood by the skilled person, e.g., for systemic or parenteral use), because the active ingredient in topically applied pharmaceuticals is subject to harsh environmental conditions in terms of changes in temperature, light exposure such as UV irradiation, humidity, mechanical stress upon application to affected areas of the skin or mucosa, and the like. Under such harsh conditions, it is important that a sufficiently high and therapeutically effective concentration of the active compound is achieved as fast as possible on the treated surfaces and in the cells forming the surfaces (e.g. the epidermal layers of the skin where herpes viruses damage affected cells). When the effective antiviral concentration in the treated area (cells, organs, e.g. the skin, or parts thereof) is reached fast, the number of herpes viruses in the treated area decreases. This reduces also the number of viruses, particularly herpes simplex viruses, in the affected area that may infect nerve cells in which these viruses may persist in a latent state, only to be reactivated by a physico-chemical stimulus, for example, changes in the cells due to psychological stress, UV-stress, or any other factor shifting the balance in the affected cell from herpes virus latency (and expression of respective virally encoded polypeptides and/or polynucleotides) to herpes virus reactivation. Reactivation causes the herpes virus to exit the state of latency and leave the cells forming the latency reservoir only to infect and productively proliferate in cells that are later destroyed, either by the viruses themselves or by host defense mechanisms, e.g. by the immune cells.

A further embodiment of the present invention is a method of treatment or suppression of the incidence of a herpes simplex virus subtype 1 or 2 infection, or suppression of transmission of a herpes simplex virus subtype 1 or 2 infection, comprising administering to a subject in need thereof an effective amount of a composition of crystalline N-[5-(aminosulfonyl)-4-methyl-1,3-thiazol-2-yl]-N-methyl-2-[4-(2-pyridinyl)-phenyl]acetamide free base hemihydrate.

The term(s) "prophylaxis and/or prevention" or similar term(s) in the art pertinent to the instant invention clearly mean to one of ordinary skill in the art the suppression or reduction of the recurrence of infection or the suppression or reduction of transmission of infection with herpes simplex virus subtype 1 or 2. In the context of the invention, the term(s) "prophylaxis and/or prevention" does not mean with, even under the broadest reasonable interpretation, the complete and total absence of any infectious virus particles or infected cells from a patient. With the background of the instant invention, such a position is reasonable in the art pertinent to the disclosed subject matter. In support of these definitions of the term(s) "prophylaxis and/or prevention" the following publications are herein incorporated by reference:

Abdool Karim, S. S., et al. (2015). Tenofovir Gel for the Prevention of Herpes Simplex Virus Type 2 Infection. N Engl. J Med 373, 530-539.

Andrei, G. et al (2011). Topical tenofovir, a microbicide effective against HIV, inhibits herpes simplex virus-2 replication. Cell Host. Microbe 10, 379-389.

Corey, L., et al., (2004). Once-daily valacyclovir to reduce the risk of transmission of genital herpes. N. Engl. J. Med. 350, 11-20.

Kleymann, G., et al. (2002). New helicase-primase inhibitors as drug candidates for the treatment of herpes simplex disease. Nat. Med. 8, 392-398.

Mertz, G. J., et al., (1985). Frequency of acquisition of first-episode genital infection with herpes simplex virus from symptomatic and asymptomatic source contacts. Sex Transm. Dis. 12, 33-39.

Reitano, M., et al., (1998). Valaciclovir for the suppression of recurrent genital herpes simplex virus infection: a large-scale dose range-finding study. International Valaciclovir HSV Study Group. J. Infect. Dis. 178, 603-610.

Schiffer, J. T., et al., (1997). Frequent genital herpes simplex virus 2 shedding in immunocompetent women. Effect of acyclovir treatment. J. Clin Invest 99, 1092-1097.

Wald, A., et al. (2014). Helicase-primase inhibitor pritelivir for HSV-2 infection. N Engl. J Med 370, 201-210.

Wald, A., et al. (2000). Reactivation of genital herpes simplex virus type 2 infection in asymptomatic seropositive persons. N. Engl. J. Med. 342, 844-850.

Zhu, J., et al. (2007). Virus-specific CD8+ T cells accumulate near sensory nerve endings in genital skin during subclinical HSV-2 reactivation. J. Exp. Med. 204, 595-603.

Gold, D., and Corey, L., MINIREVIEW Acyclovir Prophylaxis for Herpes Simplex Virus Infection. Antimicrobial Agents and Chemotherapy, March 1987, p. 361-367.

Tyring, S., Baker, D., Snowden, W., Valacyclovir for Herpes Simplex Virus Infection: Long-Term Safety and Sustained Efficacy after 20 Years' Experience with Acyclovir. The Journal of Infectious Diseases 2002; 186(Suppl 1):S40-6.

These documents support the correlation between helicase-primase inhibition and the prevention or prevention of transmission of herpes simplex virus infection as having been demonstrated in the art. Further, the above mentioned Kleymann, 2002, teaches on page 396, bottom of the left column, that recurrent disease and asymptomatic virus shedding are nearly completely suppressed by helicase-primase inhibitors, which should decrease person-to-person transmission, i.e., to effectively prevent the transmission of HSV. The above mentioned disclosure in Corey, 2004, teaches at the bottom of page 11 and on page 17, first column, that once daily suppressive therapy with valacyclovir significantly reduces the risk of transmission, i.e., prevented the transmission, of genital herpes among heterosexual, HSV-2 discordant couples. The study achieved these results by a drug that has been shown to suppress shedding of HSV type 2 (HSV-2) on genital mucosal surfaces. See the top of page 11. Further, it has been found that the frequency and amount of HSV that is shed subclinically on genital mucosal surfaces is the principal source of transmitted infections. See citations 20-22, dating back to 1997, 1998 and 1997 in the order recited. As such, an approach to reduce the frequency and amount of HSV that is shed subclinically on genital mucosal surfaces is a way to achieve prevention of transmission of herpes.

Karim, 2015, teaches at the bottom of page 530 that based on the study therein, it was shown that pericoital application of tenofovir gel reduced HSV-2 acquisition in women, i.e., prevented getting HSV. The effectiveness was a reduction of 51%. See page 534, second column. In an earlier study by the same group dating back to 2010 (see citation 6 in this reference), it was shown that pericoital application of a topical vaginal-gel formulation of tenofovir reduced HIV acquisition. While HIV is a different virus, it is not unbelievable by those of ordinary skill in the art in view of the above that a drug is able to prevent the acquisition of a viral infection. Moreover, such is explicitly confirmed to occur by Karim in the case of HSV. Gold and Corey from March 1987 support the well-known effective prophylaxis of acyclovir (i.e., viral DNA polymerase inhibitor). In addition, Tyring et al. from 2002 supports the efficacy of the prodrug valacyclovir (i.e., viral DNA polymerase inhibitor).

The person skilled in the art is aware that in case of HSV-1 and HSV-2 infection, although the viruses are present within the body due to infection, there is no symptomatic outbreak because N-[5-(amino-sulfonyl)-4-methyl-1,3-thiazol-2-yl]-N-methyl-2-[4-(2-pyridinyl)phenyl]acetamide effectively suppresses viral shedding and outbreak, which is "prophylaxis" or "suppression" against the resultant symptoms of HSV-1 and HSV-2 infection. In further support of the prophylaxis=suppression aspect of the invention, the above mentioned citations for valacyclovir (i.e. Tyring et al. 2002) and acyclovir (i.e. Gold et al. 1987) are reiterated, which also prove that it is well established that HSV infections are in normal individuals asymptomatic, and what prophylactic/suppressive therapy means in this art. Moreover, effective HSV-prophylaxis has been clinically demonstrated in human trials, and as such. In this regard, a poster from ICAAC 2014 for the HSV-2 genital herpes indication is incorporated by reference (Wald et al., 2014, supra). Finally, one of ordinary skill in the art knowns that by analogy to Tenofovir, N-[5-(amino-sulfonyl)-4-methyl-1,3-thiazol-2-yl]-N-methyl-2-[4-(2-pyridinyl)phenyl]acetamide as helicase-primase inhibitor is known to have an even higher antiviral efficacy than Tenofovir in case of HIV, and thus, for the skilled person, N-[5-(amino-sulfonyl)-4-methyl-1,3-thiazol-2-yl]-N-methyl-2-[4-(2-pyridinyl)phenyl]acetamide also would be expected to have a more pronounced prophylactic efficacy. In this regard, particularly relevant are the publications by Andrei et al. and Kleymann et al. as mentioned above. The IC50-values demonstrated therein for Tenofovir are significantly higher when compared to N-[5-(amino-sulfonyl)-4-methyl-1,3-thiazol-2-yl]-N-methyl-2-[4-(2-pyridinyl)phenyl]acetamide.

In another embodiment the present application relates to a of N-[5-(amino-sulfonyl)-4-methyl-1,3-thiazol-2-yl]-N-methyl-2-[4-(2-pyridinyl)phenyl]acetamide free base hemihydrate as defined in the preceding embodiment having a relative molecular mass of $M_r$ 411.50.

In another embodiment the present application relates to a N-[5-(amino-sulfonyl)-4-methyl-1,3-thiazol-2-yl]-N-methyl-2-[4-(2-pyridinyl)phenyl]acetamide free base hemihydrate as defined in the preceding embodiments having XRPD peaks at 5.940, 11.880 and 17.840 2theta. An example of the analysis of the free base hemihydrate is provided supra in the experimental section.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate as defined in the preceding embodiments, which has a melting point of about 204° C. to 212° C., in particular 205° C. to 211° C., particularly 206° C. to 210° C., particularly 207° C. to 209° C., e.g. around 208.2° C. The person skilled in the art knows that the determination of the melting point may be dependent on various other environmental parameters, such as humidity, etc.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate as defined in the preceding embodiments having a calculated pKa value of 4.53.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate as defined in any one of the preceding embodiments having an octanol/water partition coefficient of 0.911±0.891 at 25° C.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate, having a stability at a pH in the range of 4.5 to 7.0 of 90 to 100%.

In another embodiment the present application relates to a pharmaceutical composition comprising or that is formulated to initially comprise N-[5-(amino-sulfonyl)-4-methyl-1,3-thiazol-2-yl]-N-methyl-2-[4-(2-pyridinyl)phenyl]acetamide free base hemihydrate as defined in any one of the preceding embodiments, wherein said composition further comprises at least one pharmaceutically acceptable excipient.

In another embodiment the present application relates to a pharmaceutical composition obtainable by formulating N-[5-(amino-sulfonyl)-4-methyl-1,3-thiazol-2-yl]-N-methyl-2-[4-(2-pyridinyl)phenyl]acetamide free base hemihydrate as defined in any one of the preceding embodiments with at least one pharmaceutically acceptable excipient. The pharmaceutical composition obtainable according to the preceding embodiment may further comprise other active compounds, for example, active compounds selected from the group comprising anti-inflammatory agents, anti-viral agents, centrally and peripherally acting analgesics, (local) anesthetics, etc.

As used herein, the term "anti-inflammatory agent" refers generally to any compound or combination of compounds that, upon administration to an individual which experiencing inflammation, tends to reduce such inflammation, e.g. steroids, and non-steroidal anti-inflammatory drugs (NSAIDs) as defined also in the section supra.

As used herein "centrally and peripherally acting analgesics" comprise opioid analgesics Opioid analgesics comprise, e.g. buprenorphine or a physiologically acceptable salt or ester thereof, suitable opioid analgesics include alfentanil, allylprodine, alphaprodine, anileridine, benzylmorphine, bezitramide, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalbuphine, nalorphine, naloxone, naltrexone, normorphine, norpipanone, opium, oxycodone, oxymorphone, papaveretum, pentazocine, phenadoxone, phenomorphan, phenazocine, phenoperidine, piminodine, piritramide, profadol, propheptazine, promedol, properidine, propiram, propoxyphene, sufentanil, tilidine and tramadol. Also included are esters, salts and mixtures of any of the foregoing.

As used herein, non-opioid analgesic comprise, e.g. NSAID, a tricyclic antidepressant (e.g. amitryptyline), an anticonvulsant (e.g. gabapentin) or an antimigraine compound (e.g. sumatriptan or naratriptan). The NSAID may be a cyclooxygenase (COX) COX-1 or COX-2 inhibitor. Specific examples of NSAIDs include ibuprofen, flurbiprofen, diclofenac, indomethacin, piroxicam, ketoprofen, etodolac, diflusinal, meloxicam, aceclofenac, fenoprofen, naproxen, tiaprofenic acid, tolmetin, celecoxib and rofecoxib, and their physiologically acceptable salts and esters. Suitable salts are alkali addition salts such as the potassium or sodium salt.

In the compositions of the invention, long and short acting local and volatile anesthetics may be used that are selected from the group comprising Bupivacaine, Lidocaine, xyclocaine, tetrodotoxin (TTX), Saxitoxin (STX), etc.

In one embodiment a pharmaceutical composition obtainable by formulating the N-[5-(amino-sulfonyl)-4-methyl-1,3-thiazol-2-yl]-N-methyl-2-[4-(2-pyridinyl)phenyl]acetamide free base hemihydrate comprises a local anaesthetic.

In one embodiment a pharmaceutical composition obtainable by formulating N-[5-(amino-sulfonyl)-4-methyl-1,3-thiazol-2-yl]-N-methyl-2-[4-(2-pyridinyl)phenyl]acetamide free base hemihydrate comprises a local anaesthetic, wherein the local anaestetic is lidocaine.

In another embodiment the present application relates to the pharmaceutical composition as defined in any one of the preceding embodiments, further comprising or that is formulated to initially comprise an active selected from the group comprising selected from the group comprising anti-inflammatory agents, anti-viral agents, centrally and peripherally acting analgesics, (local) anaesthetics.

In another embodiment the present application relates to the pharmaceutical composition as defined in any one of the preceding embodiments, further comprising a sun-blockiong or UV blocking agent. In one embodiment the sun-blocking or UV-blocking agent is Octisalate. In one embodiment the sun-blocking or UV-blocking agent is titanium dioxide. In one embodiment the sun-blocking or UV-blocking agent is zinc oxide. In one embodiment the sun-blocking or UV-blocking agent is PABA. In one embodiment the sun-blocking or UV-blocking agent is homosalate. In one embodiment the sun-blocking or UV-blocking agent is trolamine salicylate.

In one embodiment the sun-blocking or UV-blocking agent is dioxybenzone. In one embodiment the sun-blocking or UV-blocking agent is sulisobenzone. In one embodiment the sun-blocking or UV-blocking agent is oxybenzone. In one embodiment the sun-blocking or UV-blocking agent is avobenzone. In one embodiment the sun-blocking or UV-blocking agent is ecasmule. In one embodiment the sun-blocking or UV-blocking agent is meradimate. In one embodiment the sun-blocking or UV-blocking agent is cinoxate. In one embodiment the sun-blocking or UV-blocking agent is octocrylene.

In another embodiment the present application relates to a pharmaceutical composition as defined in any one of the preceding embodiments, wherein said composition is selected from the group comprising topical formulations for patch administration, creams, ointments, salves, gels, skin lotions, wax formulations, lipsticks, tonics, and/or mousses, sprays, topical oils, solutions, films, etc.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate has a photostability in terms of mean percentage recovery of about 102 to 105% (103.61 to 105.11) as measured according to ICH guideline Q1B.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate has a photostability in terms of a mean purity of about 100% area/area as measured according to ICH guideline Q1B.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate as measured by HPLC in a Franz diffusion cell with a solution of 2% w/v Brij 98 in PBS as receiver fluid has a percentage recovery of about 90 to 110% (92.24 to 114.49) at t=0, about 102 to 105% (103.16 to 103.71%) at t=24 at 2 to 8° C. and about 100 to 102 (101.47 to 101.70) at 37° C. at t=25 hours, about 102 to 108 (103.57 to 106.24) at t=48 hours at 2 to 8° C., and 104 to 118 (105.42-116.70) at t=48 hours at 37° C.; about 102 to 107 (103.78 to 105.69) at t=120 hours at 2 to 8° C., and about 84 to 98 (85.85-96.40) at t=120 hours at 37° C.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of about 0.1 to about 10% w/w. The amount of the free base in the pharmaceuticals may be determined using the above described methods, e.g., HPLC, NMR spectroscopy, XRPD methods, etc.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of about 1.0 to about 7.5% w/w.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of about 2.5 to about 6.0% w/w.

In another embodiment the present application relates to the pharmaceutical composition or topical pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of about 5.0% w/w.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of 5.0% w/w, wherein the pharmaceutical composition is an ointment.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate is initially formulated to be contained at an amount of about 1.0 to about 7.5% w/w, particularly about 5.0% w/w, wherein the pharmaceutical composition is an ointment, and wherein the ointment is administered 1 to 10 times a day, or 2 to 10 times a day, or 3 to 8 times a day, or 3 to 7 times a day, or 4 to 6 times a day, or 5 times a day. It is clear that each of the concentrations may be administered in accordance with any of the above-mentioned frequencies. Each combination represents one embodiment of the invention as would be understood by a person skilled in the art.

In another embodiment the present application relates to the pharmaceutical composition as defined in any one of the preceding embodiments, wherein the N-[5-(amino-sulfonyl)-4-methyl-1,3-thiazol-2-yl]-N-methyl-2-[4-(2-pyridinyl)phenyl]acetamide free base hemihydrate is present in an amount of 1.0 to 7.5% w/w, particularly 5.0% w/w upon formulation, wherein the pharmaceutical composition is an ointment, and wherein the ointment is administered 1 to 10 times a day, or 2 to 10 times a day, or 3 to 8 times a day, or 3 to 7 times a day, or 4 to 6 times a day, or 5 times a day, and wherein the ointment is administered over a period of 2 to 14 day, 3 to 10 days, 3 to 7 days, 4 to 5 days, or over 5 days, or over 4 days. It is clear that each of the concentrations may be administered in accordance with any of the above-mentioned frequencies and each of the respective time periods. Therefore, each possible combination out of the lists of concentrations/amounts, administration frequencies and time periods represents a respective embodiment of the invention as would be understood by a person skilled in the art.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is present in an amount of 5.0% w/w, wherein the pharmaceutical composition is an ointment, and wherein the ointment is administered 5 times a day, and wherein the ointment is administered over a period of 4 days.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is present in an amount of 5.0% w/w, wherein the pharmaceutical composition is a gel, and wherein the gel is administered 5 times a day, and wherein the ointment is administered over a period of 4 days.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is present in an amount of 5.0% w/w, wherein the pharmaceutical composition is an cream, and wherein the cream is administered 5 times a day, and wherein the ointment is administered over a period of 4 days.

In another embodiment the present application relates to the pharmaceutical composition as defined in any one of the preceding embodiments, wherein N-[5-(amino-sulfonyl)-4-methyl-1,3-thiazol-2-yl]-N-methyl-2-[4-(2-pyridinyl)phenyl]acetamide free base hemihydrate is present in an amount sufficient to reach a concentration of >10 nM in the epidermis or dermis of an individual subjected to a treatment with said composition.

In another embodiment the present application relates to a N-[5-(amino-sulfonyl)-4-methyl-1,3-thiazol-2-yl]-N-methyl-2-[4-(2-pyridinyl)phenyl]acetamide free base hemihydrate as defined in the preceding embodiments for use as medicament.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment and/or prevention of herpes virus infections.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment and/or prevention of herpes virus infections, wherein said herpes viruses are selected from the order of simplex viruses.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment and/or prevention of herpes virus infections as defined in the preceding embodiments, wherein said simplex virus is selected from Herpes Simplex Virus 1 (HSV-1) and Herpes Simplex Virus 2 (HSV-2).

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in a oral pharmaceutical formulation in the treatment and/or prevention of a herpes virus infection, particularly of herpes simplex infections, in a subject in need thereof.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in a topical pharmaceutical formulation in the treatment and/or prevention of a herpes virus infection, particularly of herpes simplex infections, in a subject in need thereof.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in topical administration to a subject in need thereof, wherein said topical administration is for application to skin and mucosal surfaces, e.g. skin application in general, more specific facial application, application to the mouth, the genitals, and/or the eyes.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in systemic administration to a subject in need thereof.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of recurrent herpes labialis.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of recurrent herpes labialis selected from the group of patients showing signs of the prodromal stage of herpes labialis, patients having erythema, patients showing labial papules, patients having labial vesicles, patients with labial ulcers and/or soft crusts, patients having labial hard crusts, patients having residual labial erythema.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes genitalis.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes keratitis.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes meningitis and/or encephalitis.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes infections in the newborn.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes infections in the immunocompetent and/or immunocompromised individuals.

In another embodiment the present application relates to N-[5-(amino-sulfonyl)-4-methyl-1,3-thiazol-2-yl]-N-methyl-2-[4-(2-pyridinyl)phenyl]acetamide free base hemihydrate for use in the treatment of herpes infections in immunocompromised individuals, wherein the immunocompromised individuals are selected from the group comprising recipients of an organ transplant, individuals having an infection by another virus or bacterium, particularly an infection with HIV and/or another herpes virus, and individuals infected with a herpes simplex virus that is resistant to at least one anti-viral active.

In another embodiment the present application relates to a method of treatment and/or prophylaxis of a herpes virus infection comprising administering a N-[5-(amino-sulfonyl)-4-methyl-1,3-thiazol-2-yl]-N-methyl-2-[4-(2-pyridinyl)phenyl]acetamide free base hemihydrate to a subject in need thereof.

In another embodiment the present application relates to a method of manufacturing N-[5-(amino-sulfonyl)-4-methyl-1,3-thiazol-2-yl]-N-methyl-2-[4-(2-pyridinyl)phenyl]acetamide free base hemihydrate as defined in any of the preceding embodiments, wherein said method comprises the following steps:
 a) Mixing 4-pyridine-2yl-phenyl)-acetic acid and amionothiazole sulfonic acid amide in N-Methoylpyrrolidone (NMP);
 b) Cooling the mixture obtained in step a);
 c) Adding N-Ethyl-N'-(3-dimethylaminopropyl)-carbodiimide hydrochloride (EDC×HCl) to said mixture in b);
 d) Stirring the solution obtained in c) and addition to purified H₂O;
 e) Filtering the solution obtained in d);
 f) Washing the product cake obtained in e) with H₂O;
 g) Drying the product obtained in f);
 h) Adding purified H₂O to the solution obtained in g);
 i) Stirring the suspension obtained in h);
 j) Cooling the suspension obtained in i);
 k) Stirring the suspension obtained in j);
 l) Isolating the product by filtration from the suspension obtained in n);
 m) Washing the product obtained in o) with water;
 n) Drying the product obtained in p).

In another embodiment, the method of manufacturing N-[5-(amino-sulfonyl)-4-methyl-1,3-thiazol-2-yl]-N-methyl-2-[4-(2-pyridinyl)phenyl]acetamide free base hemihydrate as defined in any of the preceding embodiments, wherein said method comprises the following steps:
 a) Mixing 4-pyridine-2yl-phenyl)-acetic acid (5.5-6.3 kg, e.g. 5.905 kg) and amionothiazole sulfonic acid amide (5.855 kg) in N-Methoylpyrrolidone (NMP) (6.5-7.5 L, e.g. 7 L) and THF (34-39 L, e.g. 36.5 L) at a (Temperature ca. 15-25° C. e.g. 20° C.)
 b) Cooling the mixture obtained in step a) down to about −2 to 2° C., e.g. 0° C.;
 c) Adding N-Ethyl-N'-(3-dimethylaminopropyl)-carbodiimide hydrochloride (EDC×HCl)−(gradual addition, e.g. in about 4 portions of ca. 1.6 kg each time) in an amount of 6.2 to 6.8 kg, e.g., 6.538 kg) to the mixture obtained in step b);
 d) Stirring the solution obtained in step c) slowly over about 1.5-2.5 h, e.g., for 2 h, and addition to purified H₂O 70-76 L, e.g., 731);
 e) Filtering solution obtained in step d) under the pressure of 1000-1400 mbar, e.g., 1200 mbar;
 f) Washing the product cake obtained in step e) (with purified H₂O, e.g., with three washings of 2.5-3.5, e.g., 3 L each (8.5-9.5 L, e.g., 9 L));
 g) Drying the product obtained in step f) in a nitrogen stream (in vacuo at 20-250° C., e.g., 22° C., drying at higher temp such as 35-40° C. is also possible
 h) Adding purified H₂O (73+7 L) at elevated (e.g., 50-55° C.) temperature to the product obtained in step g);
 i) Stirring the suspension obtained in step h) for at least 2-6, e.g., for 4 hours;
 j) Cooling the suspension obtained in step i) to 0-10° C., e.g., at 5° C.
 k) Stirring the suspension obtained in step j) for at least 15-45 min, e.g., 30 min
 l) Isolating the product obtained in step k) by filtration under pressure of, e.g., 1200-6000 mbar
 m) Washing the product obtained in step l) with purified H₂O for about 3 times with 15-20 L, e.g. with 18 L at a pressure of about 6000 mbar;
 n) Drying the product obtained in step m)(at 60-70° C., e.g., at 65° C., e.g., in vacuo).

In another embodiment the present application relates to a pharmaceutical composition comprising N-[5-(amino-sulfonyl)-4-methyl-1,3-thiazol-2-yl]-N-methyl-2-[4-(2-pyridinyl)phenyl]acetamide free base hemihydrate obtainable in a method according to the preceding embodiment.

In another embodiment the present application relates to a pharmaceutical composition obtainable by formulation of N-[5-(amino-sulfonyl)-4-methyl-1,3-thiazol-2-yl]-N-methyl-2-[4-(2-pyridinyl)phenyl]acetamide free base hemihydrate obtainable in a method according to the preceding embodiments with at least one pharmaceutical excipient.

In another embodiment the present application relates to the use of N-[5-(amino-sulfonyl)-4-methyl-1,3-thiazol-2-yl]-N-methyl-2-[4-(2-pyridinyl)phenyl]acetamide free base hemihydrate obtainable in a method according to the preceding embodiment as medicament.

The N-[5-(aminosulfonyl)-4-methyl-1,3-thiazol-2-yl]-N-methyl-2-[4-(2-pyridinyl)-phenyl]acetamide free base hemihydrate according to the invention is a useful compound for treatment and/or prophylaxis of infectious diseases and/or prevention of transmission of infectious diseases.

The N-[5-(aminosulfonyl)-4-methyl-1,3-thiazol-2-yl]-N-methyl-2-[4-(2-pyridinyl)-phenyl]acetamide free base hemihydrate is highly active against herpes viruses and infections caused by herpes viruses and/or transmission of a herpes virus or herpes viruses. Therefore, N-[5-(aminosulfonyl)-4-methyl-1,3-thiazol-2-yl]-N-methyl-2-[4-(2-pyridinyl)-phenyl]acetamide free base hemihydrate is especially useful for the preparation of a pharmaceutical composition for the treatment and/or prophylaxis of diseases, which are caused by herpes viruses or caused by the transmission of a herpes virus or herpes viruses.

The N-[5-(aminosulfonyl)-4-methyl-1,3-thiazol-2-yl]-N-methyl-2-[4-(2-pyridinyl)-phenyl]acetamide free base hemihydrate is especially useful for the treatment and/or prophylaxis of infections, which are caused by herpes simplex viruses, or for the prevention of transmission of a herpes virus or herpes viruses.

Infections with herpes simplex viruses (HSV, subtype 1 and 2) are categorized into one of several distinct disorders based on the site of infection. Orofacial herpes simplex infection, the visible symptoms of which are colloquially called cold sores or fever blisters, affects the face and mouth. Orofacial herpes is the most common form of infection. Genital herpes is the second common form of a herpes simplex infection. Although genital herpes is largely believed to be caused by HSV-2 only, genital HSV-1 infections are increasing. Other disorders such as herpetic whitlow, herpes gladiatorum, ocular herpes (keratitis), cerebral herpes infection encephalitis, Mollaret's meningitis, neonatal herpes, and possibly Bell's palsy are also caused by herpes simplex viruses.

The N-[5-(aminosulfonyl)-4-methyl-1,3-thiazol-2-yl]-N-methyl-2-[4-(2-pyridinyl)-phenyl]acetamide free base hemihydrate is thus useful for the treatment and/or prophylaxis of infections which are caused by herpes simplex viruses and/or for the prevention of transmission of herpes simplex viruses.

The N-[5-(aminosulfonyl)-4-methyl-1,3-thiazol-2-yl]-N-methyl-2-[4-(2-pyridinyl)-phenyl]acetamide free base hemihydrate of the present invention can be combined and administered together with other actives, e.g., anti-inflammatory agents such as acetylsalicylic acid and acetaminophen, or with (local) anaesthetics, other antiviral agents, etc.

Combinations of the inventive N-[5-(aminosulfonyl)-4-methyl-1,3-thiazol-2-yl]-N-methyl-2-[4-(2-pyridinyl)-phenyl]acetamide free base hemihydrate with anaesthetics as well as pharmaceutical compositions containing such a combination are one embodiment of the present invention.

Furthermore, the inventive N-[5-(aminosulfonyl)-4-methyl-1,3-thiazol-2-yl]-N-methyl-2-[4-(2-pyridinyl)-phenyl]acetamide free base hemihydrate can be combined and can be used in combination with an anti-viral agent.

The combination of the inventive N-[5-(aminosulfonyl)-4-methyl-1,3-thiazol-2-yl]-N-methyl-2-[4-(2-pyridinyl)-phenyl]acetamide free base hemihydrate and a further active agent like an anti-inflammatory, immunomodulatory, or anti-viral agent, such as therapeutic vaccines, siRNAs, antisense oligonucleotides, nanoparticles or virus-uptake inhibitors such as n-docosanol, may be administered simultaneously in one single pharmaceutical composition or in more than one pharmaceutical composition, wherein each composition comprises at least one active agent.

The pharmaceutical compositions of the present invention can be prepared in a conventional solid and a conventional pharmaceutically-made adjuvant at suitable dosage level in a known way. Preferred preparations may be adapted for oral application. These administration forms include, for example, pills, tablets, film tablets, coated tablets, sustained release formulations, and capsules.

The pharmaceutical compositions according to the invention may comprise 1 to 70% by weight more preferably 1 to 30%, e.g. 1 to 10% by weight of N-[5-(aminosulfonyl)-4-methyl-1,3-thiazol-2-yl]-N-methyl-2-[4-(2-pyridinyl)-phenyl]acetamide free base hemihydrate (all percentage data are percentages by weight based on the weight of the pharmaceutical preparation).

A pharmaceutical composition according to the invention may be suitably formulated for systemic, oral, topic or parenteral administration.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

The compound and composition of the present invention can also be administered using patches that are applied on parts of the body of an organism, e.g. of a human being, that is infected by a herpes virus, e.g. HSV-1 and/or HSV-2. More particularly, such patches invention comprise a skin adhesive layer, a backing layer and a release liner, the adhesive layer comprising the hemihydrate of the invention and/or other active compounds dissolved in a low volatile solvent and a polymeric adhesive soluble in highly volatile solvents. The antiviral agent may be incorporated in the adhesive layer in an therapeutically and/or prophylactically effective amount, e.g., from 0.1 to 10% by weight of the dried adhesive layer, dissolved in a low volatile solvent. Solvents can be classified in function of their physical-chemical properties. Key properties, among the others, include density, viscosity, dielectric constant, dipole moment, melting and boiling point. Solvents can be broadly classified as low, middle or highly boiling according to boiling temperature at 1 bar: Low Boiling: Boiling ranges below 100° C.; Medium Boiling: Boiling ranges between 100° C. and 150° C.; High Boiling: Boiling ranges above 150° C. A low boiling solvent is a highly volatile solvent whereas a high boiling solvent is a solvent with a poor inclination to evaporate so that it can be defined as a low volatile solvent. An example of a low volatile solvent according to the invention is dimethylsulfoxide that may be present in an amount from 10 to 50% by weight of the dried adhesive layer. The adhesive polymer is selected from pectin, agar gum, acacia gum, xanthan gum, polyvinyl alcohol, polymethacrylic acid, polymethacrylate, acrylates/alkylmethacrylates copolymers, any acrylic ester copolymer, aminoalkyl methacrylate copolymer, polyvinyl pyrrolidone, cellulose or cellulose derivatives, such as hydroxypropylcellulose, hydroxyethylcellulose, or blends thereof.

The adhesive layer may be formed from a solution of the adhesive polymer in a highly volatile solvent, i.e. having a low boiling point (in the range of 40° C.-100° C.) and high vapor pressure. Said solvent is then usually evaporated during the manufacturing process even though a certain amount, up to 15% by weight, may be left in the adhesive layer after drying. The adhesive polymer or the adhesive polymer blend may be present in an amount from 20 to 50% by weight of the dried adhesive layer. The patch may further contain citric acid, succinic acid, lactic acid and esters thereof as a non polymeric crystallization inhibitors, in an amount from, e.g., 0.5 to 15% by the weight of the dried adhesive layer. The patch may also contain other excipients such as cross-linkers, penetration enhancers, plasticizers, preservatives, antioxidants, fragrances, emollients. The backing layer may be transparent, semi-occlusive or occlusive, oxygen permeable, e.g., consisting of polyurethane ether or ester film, polyethylene, ethylene vinyl acetate or polyolephine film with a MVTR (moisture vapor transmission rate) from 50 to 3500 g/m2/day and a thickness from 20 to 150 µm. The backing layer should be very flexible and soft, transparent or colored and can be occlusive or perspirating, providing a masking effect of the cold sore. Moreover, it protects the damaged skin and the viral lesions from the external contact, thus reducing the patient's pain and the possibility of further contaminations or infections, and improving the re-epithelization process. The adhesive layer is protected from the external environment through a release liner, that has to be removed before applying the patch to the site of the body interested by the viral lesions. Once the patch is applied, through the self-adhesive layer, it can be kept on-site up 6 to 24 hours, delivering the active ingredient into and across the skin. Patches are prepared by a process comprising the steps of blending the solution of adhesive polymers in highly volatile solvents together with the other components and then casting the mixture on a silicone coated liner film, before drying and the final lamination. Highly volatile solvents evaporate, leaving the adhesive film on the release liner whereas the low volatile solvent remains in the adhesive layer preventing the drug crystallization. The polymers used according to this invention are those normally used to produce pressure sensitive adhesives (PSAs) or bio-adhesive film in an organic or aqueous solution, in a concentration ranging from 20% to 80%, preferably from 20 to 50% of the composition of the adhesive mixture, while the concentrations of the highly volatile solvent are from 10% to 50%. Other components of the adhesive layer or of the reservoir layer include thickening agents, chemical permeation enhancers, non-polymeric crystallization inhibitors, flavors, surfactants, cross-linkers, buffering agents, plasticizers, preservatives, anti-oxidants, pigments. The selected solvents and polymers must of course be compatible and form an homogeneous solution which may be uniformly casted. Low boiling point solvents, i.e. high volatile solvents with boiling point not higher than 100° C., are preferably water, ethanol, methanol, isopropyl alcohol, ethyl acetate, more preferably water. Thus, it is possible to produce an anti-herpes patch, having an effective amount of the effective hemihydrate drug that can be continuously delivered to the site of application. The low volatile solvents helps to avoid crystallization by keeping dissolved the active substances in the matrix and affects the diffusivity of the drug through the matrix, to reach the skin and the site of action. The matrix must be chosen according to the physical-chemical properties of the low volatile solvents or the solvents blend. The polymer must provide a good cohesiveness to the final product. The quantitative composition of the adhesive blend is chosen in order to have an acceptable film in terms of thickness, cohesion properties, mechanical resistance, skin adhesion, peel properties and handling. The polymer blend range in the dry matrix is 5%-50%, most preferably 20%-35%, solubilized in a low boiling point solvent or solvent mixture. The solvent percentage ranges from 20% to 70%, preferably from 35% to 55%, in the mixture that has to be casted to produce the adhesive layer or the reservoir layer. In the dry matrix the amount of low boiling point solvent must not exceed 15% by weight. The low volatile solvents, instead, are included in the dry matrix, entangled in the polymer and dissolving the active ingredients. The amount of these solvents in the dry state is in the range 10%-50%, but preferably in the range 30%-55%.

The following examples are included to demonstrate preferred embodiments of the invention. It should be appreciated by those of skill in the art that the techniques disclosed in the examples, which follow, represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXPERIMENTS

Example 1—Identification of N-[5-(aminosulfonyl)-4-methyl-1,3-thiazol-2-yl]-N-methyl-2-[4-(2-pyridinyl)-phenyl]acetamide Free Base Hemihydrate The N-[5-(aminosulfonyl)-4-methyl-1,3-thiazol-2-yl]-N-methyl-2-[4-(2-pyridinyl)-phenyl]-acetamide free base hemihydrate was identified by extensive polymorph hydrate screening starting from N-[5-(aminosulfonyl)-4-methyl-1,3-thiazol-2-yl]-N-methyl-2-[4-(2-pyridinyl)-phenyl]-acetamide on the monohydrate form of the above compound according to Formula (I) in order to identify a suitable or the most stable form of said compound in formula I (the free base of the mesylate of N-[5-(aminosulfonyl)-4-methyl-1,3-thiazol-2-yl]-N-methyl-2-[4-(2-pyridinyl)-phenyl]-acetamide):

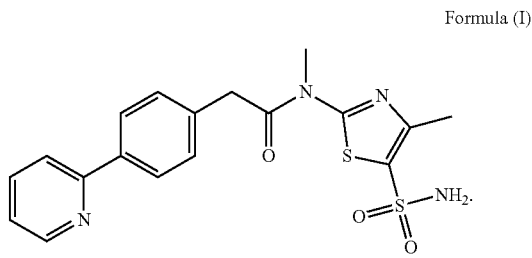 [SMILES: Cc1nc(N(C)C(=O)Cc2ccc(-c3ccccn3)cc2)sc1S(N)(=O)=O]

Formula (I)

Several polymorph/solvates were identified and characterized by single XRPD and DSC, Karl Fischer water content. Surprisingly, the free base hemihydrate was the only stable polymorph. The polymorphism screening was performed using an approach to find kinetically preferred polymorphs as well as thermodynamically preferred or in other words more stable polymorphs. The kinetically preferred polymorphs were examined using evaporation and cooling crystallisations, the thermodynamically preferred polymorphs were examined using slurry type experiments. The nomenclature used for the categorisation of different forms is as follows: the forms are typically chronologically assigned to capital letters. The first material isolated and analysed by X-Ray powder diffraction is named form A. For the screening two different lots of starting materials were used, both having the same form according to XRPD: Form B, which is a monohydrate.

Evaporation Screening Method

For the evaporation experiments approximately 100 mg monohydrate Form B was suspended/dissolved in each of the solvents listed (max. 4 mL) in Table 1 below. Solvents were chosen to have a high diversity, e.g. in polarity, protic/aprotic, acceptability according to ICH guidelines, and assuming a certain solubility of the mesylate free base. Experiments where no dissolution occurred at room temperature were heated to maximum 60° C. and in case still no dissolution occurred were filtered at elevated temperature to obtain a more concentrated starting solution. The solutions were evaporated in a drying oven starting at 25° C. and 850 mbar with a constant flow of nitrogen decreasing vacuum after 3 days 750 mbar; after 5 days remaining solutions were concentrated using a nitrogen stream. The resulting solids were examined visually and in cases where a sufficient amount of solid was obtained X-ray powder diffraction was performed. A total of 15 different polymorph forms were identified (including initial form B)

Cooling and Precipitation Screening Method:

For the cooling experiments approximately 100 mg of monohydrate polymorph Form B was slurried in each of the solvents listed below (max. 4 mL) and the resulting suspensions heated to maximum 65° C. In case still no dissolution occurred the suspensions were filtered or decanted and then the mother liquor shock cooled in an ice bath (ca. −10° C.) until a suspension was obtained. After approximately 15 minutes at low temperature, solutions without spontaneous nucleation were treated with anti-solvent as indicated in Table 2 below. Resulting suspensions were filtered, the solids slightly dried and tested by XRPD.

TABLE 1

Evaporation screening results. Form X indicates additional reflexes that do not correspond to any other observed form.
Experiment: NE-023931-Z-0-3 (A-Serie)
Crystallisation by evaporation BXR2KVE/001123
Ca. 100 mg dissolved in 3 mL solvent. In case no solution was obtained, heated to 50° C. and solids were filtered off and mother liquors evaporated during max. one week.

| Exp. | Solvent | Optical impression | Comment | Form |
|---|---|---|---|---|
| A1_1 | TBME | needles | | D |
| A1_2 | THF | wax | | B |
| A1_3 | 2-MeTHF | thin needles | | E |
| A1_4 | dioxane | thin needles | | E |
| A1_5 | acetone | hair | | (B) E |
| A1_6 | MEK | hair | | E (X) |
| A1_7 | MIBK | hair | | A C |
| A1_8 | water | — | no solid | — |
| A1_9 | methanol | needles | | F |
| A1_10 | ethanol | thin needles | | G |
| A2_1 | 2-Propanol | thin needles | | E |
| A2_2 | 1-Propanol | thin needles | | E X |
| A2_3 | trifluoroethanol | cotton-like | | E |
| A2_4 | 1-butanol | thin needles | | E |
| A2_5 | methyl acetate | thin needles | | E |
| A2_6 | Ethyl acetate | thin needles | | E |
| A2_7 | isopropyl acetate | hair | | A |
| A2_8 | ACN | hair | | E X |
| A2_9 | DMSO | resin | | — |
| A2_10 | Chorobenzene | thin needles | | E |
| A3_1 | DCM | — | no solid | EDA |
| A3_2 | Toluene | cotton-like | no solid | — |
| A3_3 | 1-Methoxy-2-propanol | thin needles | | A (C) |
| A3_4 | DCM/MeOH 7/3 | needles | | H |
| A3_5 | EtOH/Water 8/2 | needles | | C |
| A3_6 | ACN/Water 8/2 | thin needles | | C |
| A3_7 | Toluene/THF 8/2 | needles | | I |

TABLE 2

Cooling/precipitation screening results. Tmax in ° C.

| Exp. | Solvent | Volume (mL) | Solution (60° C.) | Anti-solvent | Volume (mL) | Form |
|---|---|---|---|---|---|---|
| B1_1 | THF/water 88/12 | 1 | yes | water | 4 | L |
| B1_2 | THF/water 75/25 | 1 | yes | water | 4 | A |
| B1_3 | MEK | 5 | no | TBME | 3 | E |
| B1_4 | methanol | 6 | no | — | — | F X |
| B1_5 | ethanol | 6 | no | — | — | G |
| B1_6 | isopropanol | 6 | no | — | — | M |

TABLE 2-continued

Cooling/precipitation screening results. Tmax in °C.

| Exp. | Solvent | Volume (mL) | Solution (60° C.) | Anti-solvent | Volume (mL) | Form | |
|---|---|---|---|---|---|---|---|
| B1_7 | Ethyl acetate | 5 | no | — | — | E | |
| B1_8 | ACN | 5 | no | — | — | N | |
| B1_9 | DCM | 6 | no | — | — | C | |
| B1_10 | THF | 2 | yes | TBME | 5 | A | E |
| B2_1 | toluene/MeOH 8/2 | 5 | no | — | — | F | |
| B2_2 | MeOH/water 6/4 | 5 | no | — | — | O | |
| B2_3 | DCM/MeOH 7/3 | 5 | no | — | — | H | |
| B2_4 | ACN/water 8/2 | 5 | no | — | — | N | |
| B2_5 | EtOAc wet | 5 | no | — | — | L | |

Slurry Screening Method

The slurry experiments were performed by taking approximately 100 mg of monohydratic Form B and slurrying in each of the solvent mixtures as detailed in the table below using a magnetic stir bar. As the focus was set on hydrate forms mostly aqueous solvent mixtures were used as shown in Table 3.

TABLE 3

Slurry screening results

| Experiment | Solvent | Optical impression | Form | |
|---|---|---|---|---|
| C1_1 | THF | | B | E |
| C1_2 | THF/water 2/8 | | (B) | E |
| C1_3 | THF/water 4/6 | | (C) | E |
| C1_4 | THF/water 6/4 | | (B) | E |
| C1_5 | water | | C | (X) |
| C1_6 | MeOH/water 4/1 | | F | X |
| C1_7 | MeOH/water 1/1 | Coarse | C | |
| C1_8 | acetone/water 1/2 | | B | |
| C1_9 | IPA/water 3/1 | | E | |
| C1_10 | EtOH/water 2/1 | Coarse | C | |
| C2_1 | EtOAc wet | | (B) | E |

The identified forms were then further characterized by several methods: XRPD, Optical microscopy, $^1$H-NMR, DSC, TGA, and DVS. The physical characterization of the free base hemihydrate referred to herein was performed using compendial methods as per European Pharmacopoeia (Ph. Eur.) and/or the U.S. Pharmacopeial Convention (USP).

Melting Point by DSC
Principle: Differential scanning calorimetry with power compensation
Equipment: DSC-systems (DSC 822e-Mettler Toledo)/analytical micro balance
Procedure: An accurately weighed amount of sample (typically 1-5 mg), is placed in a clean and dry aluminium crucible and closed with an aluminium cap with a hole. A second crucible is the reference crucible.
Conditions:
starting temperature: 20° C.
heating rate: 10° C./min
final temperature: 300° C.
atmosphere: N2 (flow 20 mL/min)
TGA Volatile Components
Principle: Thermogravimetry.
Equipment: TGA 851e apparatus comprising oven, oven temperature sensor and sample temperature sensor/aluminium oxide pan/analytical micro balance.
Procedure: An empty aluminium oxide pan is used to collect the background curve. Afterwards an accurately weighed amount of sample (typically 10 mg) is placed in a clean and dry pan.
The measurement is done as described in the analytical instruction.
Conditions:
starting temperature: 25° C.
heating rate: 5° C./min
final temperature: 300° C.
atmosphere: N2 (flow 50 mL/min)
$^1$H NMR
Equipment: Bruker AVANCE 400 MHz
Solvent: DMSO-D6 or CDCl3
Internal Standard: Tetramethylsilane (TMS) or solvent peak
Decoupling: Inverse gate decoupling
Assays: Assays are determined using a macro for the ACD/Spec Manager 9 by comparison of integration areas of the compound with those of an internal standard (typically hydrochinondimethylether) are compared.
Light Microscopy with Hot Stage Equipment:
Olympus BX41 with Di-Li 5MP camera and grab & measure software
Hotstage Mettler Toledo FP90 with FP 82 heating table
Method: Samples are prepared with brushes onto object holders. Observation is done using unpolarised light or polarised light using two polarisation filters at 40, 100, 200 or 400× magnification. Pictures are taken by software and exported as JPEG, scale is only approximate and not validated.
X-Ray Powder Diffraction (XRPD)
Equipment: MiniFlex by Rigaku Corporation using silicon low background sample holders (diameter 24 mm, pit 0.2 mm); Tube: Cu, 1=1.54056 Å, 15 kV
Method: Angle: 2θ=2° to 2θ=40°; Sampling width 0.02 [2θ]; Measurement time: 75 minutes.
Preparation: Samples were ground with mortar and pestle when a sufficient amount was isolated; this leads to more consistent results, less preferred orientation and better handling of material with huge particle size. Solid positioned on sample holder prepared with grease and flattened with a disc of glass.
HPLC
The method below is a laboratory method to quickly determine concentration and is different to the method used to track synthesis of C-019998.
Column: Phenomenex Luna 3 μm C18 (50×4.6 mm), Detection: DAD detector, recording at 240 nm; Diluent: 0.2 mg/mL in ACN/H2O 1:9+1% TFA; Eluents: A="H$_2$O+ 0.05% CF$_3$COOH"; B="CH$_3$CN+0.05% CF$_3$COOH"; Method: Injection: 5 μL; Flow: 1.0 mL/min

| Min | Eluents | |
|---|---|---|
| 0.00 | % A = 90.0 | |
| | % B = 10.0 | |

| Min | Eluents |
|---|---|
| 0.10 | % A = 90.0 |
|  | % B = 10.0 |
| 10.1 | % A = 10.0 |
|  | % B = 90.0 |
| 12.1 | % A = 10.0 |
|  | % B = 90.0 |
| 12.1 | % A = 90.0 |
|  | % B = 10.0 |
| 15.1 | % A = 90.0 |
|  | % B = 10.0 |

The screening identified a total of 14 different forms; an additional form was found during scale-up phase. Of most forms identified by XRPD sufficient amounts to perform additional analytics were still available from the screening phase. First microscopy (habit, aspect) and NMR (structure confirmation, residual solvents) were performed and if more material was available also DSC and TGA were performed to get an idea how residual solvents were included and what kind of form conversion would happen. The following tables show a summary of analytical data that was collected after screening phase as well as during scale-up phase.

TABLE 4

Overview on forms identified during screening/scale-up phase, sample used for reference XRPD pattern, number of occurrences (hits) during screening and solvent used for preparation of characterised sample.

| Form | Reference for XRPD | LIMS Task/ID | hits (#) | Character-ised | Solvent |
|---|---|---|---|---|---|
| A | A2_7 | 304832227 | 6 | A2_7 | iPrOAc |
| B | BXR2KVE | 304760695 | 7 | BXR2KVE | unknown |
| C | NE-023932-A-3-30 stabi 1#1 | 304781778 | 9 | A-3-30 cryst | THF/water |
| D | A1_1 | 304832215 | 1 | A1_1 | TBME |
| E | A1_3 | 304832219 | 24 | A2_6 | EtOAc |
| F | A1_9 | 304832229 | 3 | B2_1 | MeOH |
| G | A1_100 | 304832231 | 2 | A1_10 | Ethanol |
| H | A3_4 | 304832255 | 2 | A3_4 | DCM/MeOH |
| I | A3_7 | 304832261 | 1 | A3_7 | Toluene/THF |
| K | A3_10 | 304832267 | 1 | A3_10 | TBME/MeOH |
| L | B1_1 | 304848202 | 2 | B2_5 | EtOAc wet |
| M | B1_6 | 304848212 | 1 | B1_6 | IPA |
| N | B1_8 | 304848216 | 2 | B1_8 | ACN |
| O | B2_2 | 304848224 | 1 | B2_2 | MeOH/water |
| P | NE-023931-Z-0-3 VV1 | 304885619 | — | Z-0-3-VV1 | TBME |

TABLE 5

Overview on 1H NMR results of different forms of monohydrate Form B.

| Form | Character-ised | Solvent | NMR** | NMR % w/w |
|---|---|---|---|---|
| A | A2_7 | iPrOAc | no solvent | — |
| B | BXR2KVE | ? | no solvent | — |
| C | A-3-30 cryst | THF/water | no solvent | — |
| D | A1_1 | TBME | <0.1 eq* | 2.19 (TBME) |
| E | A2_6 | EtOAc | 0.29 eq EtOAc | 5.94 (EtOAc) |
| F | B2_1 | MeOH | 0.90 eq MeOH | 6.70 (MeOH) |
| G | A1_10 | Ethanol | 0.93 eq EtOH | 9.61 (EtOH) |
| H | A3_4 | DCM/MeOH | 0.96 eq MeOH/ 0.4 eq DCM | 7.1/7.3 (MeOH/DCM) |
| I | A3_7 | Toluene/THF | 0.02 eq toluene* | 0.55 (toluene) |
| K | A3_10 | TBME/MeOH | 0.72 eq MeOH | 5.44 (MeOH) |
| L | B2_5 | EtOAc wet | <0.1 eq | — |
| M | B1_6 | IPA | 1.1 eq IPA | 14.18 (IPA) |
| N | B1_8 | ACN | 0.83 eq ACN | 7.79 (ACN) |
| O | B2_2 | MeOH/water | 0.75 eq MeOH | 5.76 (MeOH) |
| P | Z-0-3-VV1 | TBME | 0.42 eq TBME | 8.25 (TBME) |

**DMSO-D6 was used as solvent and might contain large amounts of water so that no estimation of water content is possible.

TABLE 6

Overview of thermal analysis results of different forms of monohydrate Form B.

| Form | Character-ised | Solvent | TGA % w/w (temp.) | DSC (+endo, −exo) [° C.] | solvents (TGA + NMR) |
|---|---|---|---|---|---|
| A | A2_7 | iPrOAc | 0 | mp: 208.8 | — |
| B | BXR2KVE | unknown | 3.76 (20-40° C.) | +54, +130, −136, mp: 207.3 | 3.8% water |
| C | A-3-30 cryst | THF/water | 2.14 (80-140° C.) | +140(b), mp: 208.2 | 2.14% water |
| D | A1_1 | TBME | n/a | n/a | n/a |
| E | A2_6 | EtOAc | 6.10 (120-160° C.) | +142 (d), mp: 205.8(d) | 5.9% EtOAc |
| F | B2_1 | MeOH | 8.72 (40-130° C.) | +121, mp: 207.6 | 6.7% MeOH, 2% water |
| G | A1_10 | Ethanol | 9.97 (60-120° C.) | +120, mp: 206.8 | 9.6% EtOH, 0.3% water |
| H | A3_4 | DCM/MeOH | 14.89 (60-100° C.) | +92, mp: 205.8 | 7.1% MeOH/7.3% DCM |
| I | A3_7 | Toluene/THF | n/a | n/a | 0.6% toluene |
| K | A3_10 | TBME/MeOH | n/a | n/a | 5.4% MeOH |
| L | B2_5 | EtOAc wet | 8.95 (40-140° C.) | +103, mp: 207.6 | 8.9% water |
| M | B1_6 | IPA | n/a | n/a | 14.2% IPA |
| N | B1_8 | ACN | 8.31 (110-160° C.) | +145, +159, mp: 208.4 | 7.8% ACN, 0.5% water |
| O | B2_2 | MeOH/water | n/a | n/a | 5.8% MeOH |
| P | Z-0-3-VV1 | TBME | 8.22 (60-100° C.) | +93, mp: 202.7 | 8.2% TBME |

For TGA weight loss a temperature range is given. The DSC data shows endothermic and exothermic events as well as melting points; the temperature given represents the peak temperature. The collected data about solvent content together with TGA data was used to exclude a series of forms from further characterisation work as these forms were assumed to be solvates or at least forms that intensively include solvents. The following forms were excluded:

Form B: a monohydrate releasing water already slightly above ambient temperature.
Form F: a methanol solvate.
Form G: an ethanol solvate.
Form H: a form including methanol and dichloromethane in large amounts.
Form K: probably a methanol solvate.
Form L: a dihydrate, which releases water from 40 to 160° C.
Form M: an isopropanol solvate.
Form N: an acetonitrile solvate
Form O: a methanol solvate.
Form P: a TBME solvate From the remaining forms only Form C, i.e. N-[5-(aminosulfonyl)-4-methyl-1,3-thiazol-2-yl]-N-methyl-2-[4-(2-pyridinyl)-phenyl]-acetamide hemihydrate was taken into the next phase as the only hydrate form. Form E cannot be clearly assigned to be a solvate or non-solvated form but is assumed to be a channel solvate. In case form E is assumed to be a non-solvated form that includes the solvents currently present in the crystallization experiment, it has to be seen as quite stable form concurring with form A that is the most stable non-solvate. In this case it highly depends on the composition of the crystallization system; one might conclude that form A probably would not convert to form A when no solvents are present. Some forms contain solvents from 0.5 to 1 equivalents and were assigned as solvates. According to DSC/TGA the hydrates seem to have a clear order of stability: C>L>B but experiments to produce form L (dihydrate) indicate that form L is quite unstable. Most of the forms provide sufficient room in the crystal lattice to include water or a solvent. Inclusion of water in the potential gaps and reduction of risk of high levels of residual solvents is preferable.

Advantageously, the hemihydrate form C provides sufficient stability with low risk of dehydration when being stored in a closed container at ambient temperature.

Example 2

XRPD-Analysis of N-[5-(aminosulfonyl)-4-methyl-1,3-thiazol-2-yl]-N-methyl-2-[4-(2-pyridinyl)-phenyl]-acetamide Free Base Hemihydrate Sample preparation: In order to acquire a powder diffraction pattern of the obtained solid, approximately 20 mg of the white powder sample was prepared in standard sample holders using two foils of polyacetate and subsequently analysed as described below.

Data collection: Powder diffraction patterns were acquired on a Bruker D8 Advance Series 2Theta/Theta powder diffraction system using CuKα1-radiation (1.54060 Å) in transmission geometry. The system is equipped with a VĂNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0 and Microsoft Excel. Samples were measured in 20-minute scans in a range from 4° to 40° in 2θ (step size: 0.016°).

Powder X-Ray Diffraction Patterns

The Powder X-Ray Diffraction Patterns of the free base hemihydrate (FIG. 1) is that of a highly crystalline solid. Characteristic peaks are labelled. Table 7 below shows the peak list of the PXRD pattern of the free base hemihydrate represented in FIG. 1. The characteristic peaks have been highlighted in bold face.

TABLE 7

| 2θ (°) | d (Å) | Rel. Int. % |
|---|---|---|
| 5.9 | 14.99 | 11.6 |
| 10.1 | 8.78 | 4.6 |
| 11.0 | 8.00 | 3.4 |
| 11.7 | 7.55 | 13.1 |
| 11.9 | 7.45 | 6.4 |
| 12.6 | 7.00 | 4.4 |
| 13.3 | 6.67 | 4.7 |
| 13.6 | 6.51 | 5.1 |
| 14.0 | 6.34 | 3.7 |
| 15.5 | 5.71 | 55.6 |
| 17.4 | 5.10 | 3.9 |
| 17.9 | 4.96 | 10.2 |
| 18.7 | 4.74 | 7.8 |
| 19.0 | 4.68 | 3.6 |
| 19.3 | 4.60 | 3.6 |
| 20.0 | 4.44 | 100 |
| 20.3 | 4.37 | 5.1 |
| 20.9 | 4.26 | 49.1 |
| 21.1 | 4.20 | 9.2 |
| 21.6 | 4.11 | 3.9 |
| 22.1 | 4.01 | 15.7 |
| 23.3 | 3.81 | 3.1 |
| 24.0 | 3.70 | 46.3 |
| 24.5 | 3.64 | 3.8 |
| 24.8 | 3.59 | 8.2 |
| 25.5 | 3.49 | 67.5 |
| 26.9 | 3.32 | 54.5 |
| 27.4 | 3.25 | 17.8 |
| 28.1 | 3.17 | 4.4 |
| 28.9 | 3.09 | 51.6 |
| 29.4 | 3.04 | 3.6 |
| 29.5 | 3.02 | 3.9 |
| 30.0 | 2.98 | 6.6 |
| 30.7 | 2.91 | 6.5 |
| 31.3 | 2.85 | 2.9 |
| 31.5 | 2.83 | 2.3 |
| 32.3 | 2.77 | 1.8 |
| 32.7 | 2.74 | 9.8 |
| 33.3 | 2.69 | 5.6 |
| 33.6 | 2.66 | 1.7 |
| 34.2 | 2.62 | 4.4 |
| 34.8 | 2.58 | 2.1 |
| 35.1 | 2.56 | 1.8 |
| 35.7 | 2.51 | 3 |
| 36.4 | 2.47 | 2.9 |
| 36.7 | 2.45 | 1.7 |
| 37.2 | 2.42 | 2.9 |
| 37.5 | 2.40 | 5.6 |
| 37.7 | 2.39 | 4.2 |
| 38.0 | 2.37 | 2.2 |
| 38.4 | 2.34 | 1.9 |
| 38.7 | 2.33 | 3.9 |
| 39.2 | 2.30 | 4.4 |

Solubility and Relative Stability of Forms.

For analysis of the form stability, hydrates and solvent free forms were investigated separately.

Hydrates

The hemihydrate Form C was isolated on larger scale. The starting material for the screening (Form B) was a monohydrate. Additionally a potential dihydrate (form L) was identified. DVS indicated that the monohydrate (Form B) seems to release and adsorb water more rapidly than Form C (hemihydrate). During the DVS experiment time (<600 min for Form C) almost no change at 25° C. was observed. To extend the exposure to different relative humidity (RH) values small vials with solid/saturated solutions were loaded with an open pan of Form C on top and the sealed vials kept for 5 days (see the data below for different humidity levels). The resulting hemihydrate was checked by XRPD and all samples confirmed to be Form C (the free base hemihydrate).

TABLE 8

Salt and solutions to simulate different relative humidity values

| Salt (solution) | Targeted relative humidity |
|---|---|
| KOH (solid) | <5% RH |
| KOH (sat.) | 10% RH |
| KOAc (sat) | 20% RH |
| $K_2CO_3$ (sat) | 43% RH |
| $NaCr_2O_7$ (sat) | 58% RH |
| $NH_4Cl$ (sat) | 80% RH |
| water | 100% RH |

Combined with the results from TGA and DSC where approximately 60° C. difference between dehydration temperatures can be observed for forms B and C the stability for the hemihydrate is much higher compared to the other hydrate forms.

Detailed Characterization of the Hemihydrate Form C:

General properties of N-[5-(aminosulfonyl)-4-methyl-1,3-thiazol-2-yl]-N-methyl-2-[4-(2-pyridinyl)-phenyl]-acetamide hemihydrate Table 9:

TABLE 9

| Property | Result |
|---|---|
| Appearance (color, physical form) | White to yellow solid |
| Melting point | About 205-210° C. (under conditions used herein approx. 208.2° C.) |
| Octanol/water partition coefficient | 0.911 ± 0.891 (25° C.) |
| $pK_a$ value | 4.53 (calculated); 4.6 (photometric titration) |
| Hygroscopicity | Not hygroscopic |
| Polymorphism | A polymorphism screening was performed on two batches of the N-[5-(aminosulfonyl)-4-methyl-1,3-thiazol-2-yl]-N-methyl-2-[4-(2-pyridinyl)-phenyl]-acetamide monohydrate (Form B). Kinetically preferred polymorphs were examined using evaporation and cooling crystallizations, thermodynamically preferred polymorphs were examined using slurry type experiments. Several crystal forms have been observed for the free base. The most stable form is the hemihydrate (form C), which is used as drug substance. |

Figure 2:
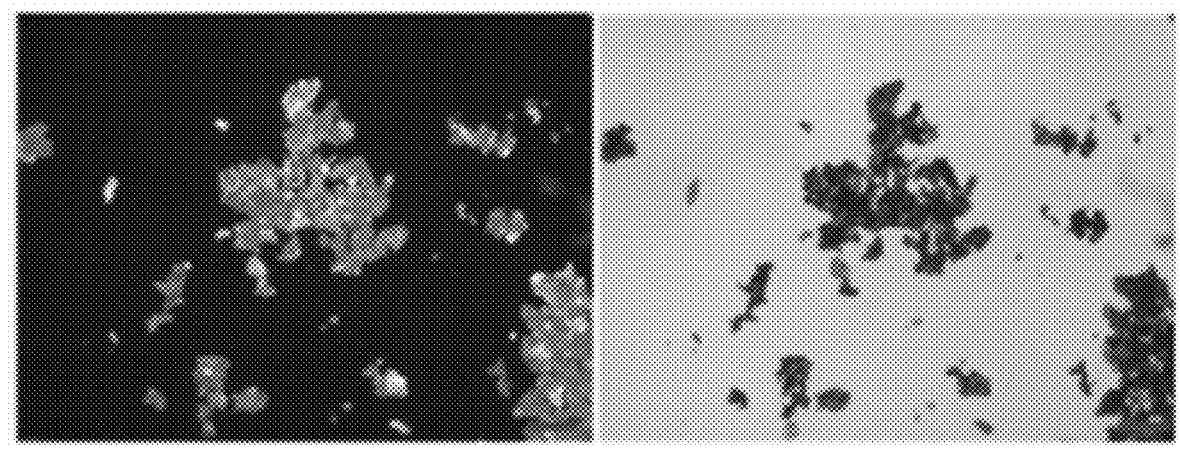

Microscope pictures are shown in FIG. 2 demonstrating that Form C consists of rod-like crystals showing birefringence under the microscopy.

A crystallization screening was carried out using 3 different solvents (ethanol/water 8:2, acetonitrile/water 8:2 and THF/water 9:1), in order to obtain crystals suitable for single crystal X-ray diffraction analysis. General procedure: The hemihydrate of N-[5-(aminosulfonyl)-4-methyl-1,3-thiazol-2-yl]-N-methyl-2-[4-(2-pyridinyl)-phenyl]-acetamide free base hemihydrate)(50 mg) was dissolved in the minimum quantity of the solvent at 60° C., and the solution was cooled to room temperature and slowly evaporated. Results: Single crystals were obtained using ethanol/water and acetonitrile/water as solvents. However, only crystals obtained in ethanol/water corresponded to form C (P067-01-EOH-H2O-01). A sample was characterized by single crystal X-ray diffraction (SCXRD). The asymmetric unit contains two independent molecules of the organic compound and one molecule of water. The measured crystal in the below Table 10 corresponds to a hemihydrate as shown in FIG. 1.

TABLE 10 characterized by single crystal X-ray diffraction (SCXRD) 2theta (deg.)

| Peak no. | 2theta | Flex Width | d-value | Intensity | I/Io |
|---|---|---|---|---|---|
| 1 | 5.940 | 0.188 | 14.8665 | 13414 | 100 |
| 2 | 11.880 | 0.188 | 7.4433 | 10732 | 80 |
| 3 | 13.580 | 0.188 | 6.5151 | 1704 | 13 |
| 4 | 15.580 | 0.259 | 5.6829 | 2247 | 17 |
| 5 | 17.380 | 0.165 | 5.0982 | 456 | 4 |
| 6 | 17.840 | 0.188 | 4.9678 | 10645 | 80 |
| 7 | 18.640 | 0.165 | 4.7563 | 386 | 3 |
| 8 | 20.180 | 0.188 | 4.3967 | 1055 | 8 |
| 9 | 20.860 | 0.188 | 4.2549 | 915 | 7 |
| 10 | 21.140 | 0.165 | 4.1992 | 295 | 3 |
| 11 | 22.240 | 0.306 | 3.9939 | 430 | 4 |
| 12 | 23.980 | 0.212 | 3.7079 | 401 | 3 |
| 13 | 25.460 | 0.188 | 3.4956 | 604 | 5 |
| 14 | 26.000 | 0.188 | 3.4242 | 440 | 4 |
| 15 | 26.860 | 0.188 | 3.3165 | 776 | 6 |
| 16 | 27.420 | 0.165 | 3.2500 | 266 | 2 |
| 17 | 28.860 | 0.235 | 3.0911 | 631 | 5 |
| 18 | 29.980 | 0.212 | 2.9781 | 660 | 5 |
| 19 | 30.740 | 0.212 | 2.9062 | 393 | 3 |
| 20 | 31.520 | 0.212 | 2.8360 | 403 | 3 |
| 21 | 34.120 | 0.235 | 2.6256 | 390 | 3 |
| 22 | 36.360 | 0.353 | 2.4688 | 308 | 3 |
| 23 | 37.440 | 0.212 | 2.4001 | 286 | 3 |
| 24 | 38.460 | 0.235 | 2.3387 | 298 | 3 |

Synthetic Route—Manufacture of N-[5-(aminosulfonyl)-4-methyl-1,3-thiazol-2-yl]-N-methyl-2-[4-(2-pyridinyl)-phenyl]-acetamide Free Base Hemihydrate The starting materials (4-pyridine-2-yl-phenyl)-acetic acid (PP-acetic acid; C-023930) and aminothiazole sulfonic acid amide (C-023936) are coupled using standard reaction conditions (N-Ethyl-N'-(3-dimethylaminopropyl)-carbodiimide hydrochloride (EDC×HCl), tetrahydrofuran (THF)/N-methylpyrrolidone (NMP) to deliver N-[5-(aminosulfonyl)-4-methyl-1,3-thiazol-2-yl]-N-methyl-2-[4-(2- pyridinyl)-phenyl]-acetamide free base hemihydrate (C-023931). To obtain the hemihydrate, N-[5-(aminosulfonyl)-4-methyl-1,3-thiazol-2-yl]-N-methyl-2-[4-(2-pyridinyl)-phenyl]-acetamide hemihydrate free base is recrystallized from THF/water. A flowchart showing the synthesis of N-[5-(aminosulfonyl)-4-methyl-1,3-thiazol-2-yl]-N-methyl-2-[4-(2-pyridinyl)-phenyl]-acetamide is provided in below in the reaction scheme below 1.

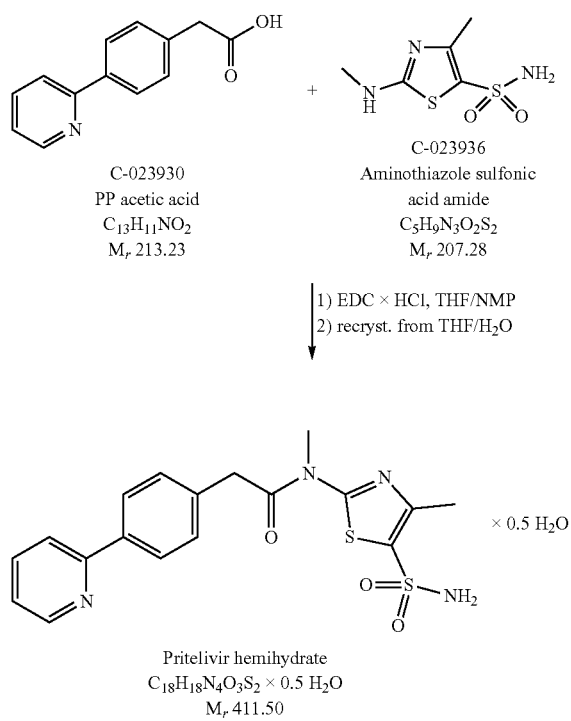 [SMILES: O=C(O)Cc1ccc(-c2ccccn2)cc1 ; CNc1nc(C)c(S(N)(=O)=O)s1 ; Cc1nc(N(C)C(=O)Cc2ccc(-c3ccccn3)cc2)sc1S(N)(=O)=O]

Description of the Manufacturing Process of N-[5-(aminosulfonyl)-4-methyl-1,3-thiazol-2-yl]-N-methyl-2-[4-(2-pyridinyl)-phenyl]-acetamide Free Base Hemihydrate PP-acetic acid and aminothiazole sulfonic acid amide are mixed in THF/NMP, the mixture is cooled and then EDC× HCl is added in portions. The reaction mixture is stirred for several hours, and then added slowly to purified water. The suspension is stirred and filtered; the product cake is washed with purified water and dried at room temperature in a nitrogen stream and then under vacuum. Purified water is added slowly at elevated temperature, the suspension is stirred for several hours. The suspension is cooled to 5° C. and stirred further for several hours. The product is isolated by filtration and washed with purified water. The product is dried at 65° C. under vacuum until the criterion for water content is reached. A major advantage of the synthesis of free base of N-[5-(aminosulfonyl)-4-methyl-1,3-thiazol-2-yl]-N-methyl-2-[4-(2-pyridinyl)-phenyl]-acetamide hemihydrate is the absence impurities related to the presence of mesylate ester that might be present in the N-[5-(aminosulfonyl)-4-methyl-1,3-thiazol-2-yl]-N-methyl-2-[4-(2-pyridinyl)-phenyl]-acetamide mesylate.

According to the $^1$H-NMR spectrum of the free base hemihydrate Form C (FIG. 3) solvents are not visible.

The infrared spectroscopic data obtained are consistent with the chemical structure as demonstrated by assignment of band maxima to the functional groups of the molecule (FIG. 9).

Comparative Solubility of Free Base and Free Base Hemihydrate in Individual Excipients Free base hemihydrate exhibited similar or slightly higher solubility of in the principal solvents compared to free base; therefore any physicochcemical data for free base can be extrapolated to free base hemihydrate.

Saturated solubility (% w/w) of two forms of pritelivir (batches BXR2KVE for the free base and M023862-CA15-033 for pritelivir hemihydrate) in PEG 400 and propylene glycol, mean (range, n=3) are shown in Table 11 below.

TABLE 11

| | Saturated solubility (% w/w) of pritelivir | | |
|---|---|---|---|
| Solvent | pritelivir free base* (BXR2KVE, Test Item 1) | pritelivir free base (BXR2KVE, Test Item 1) | pritelivir hemihydrate (M023862-CA15-033, Test Item 2) |
| PEG 400 | 7.87 (7.83-7.91) | 3.30 (1.54-4.65) | 7.87 (7.80-7.92) |
| Propylene glycol | 2.84 (2.74-2.94) | 0.20 (0.20-0.21) | 0.59 (0.58-0.60) |

Photostability Testing of Current Clinical Formulation O1v3

The formulation O1v3 comprises the following excipients and active ingredients (in % w/w)

| | |
|---|---|
| PEG 400 (super refined) | 55.00 |
| 0.5M NaOH/HCl | to make up pH 4-5 |
| PEG 400 (super refined) (second addition) | q.s 100%, so that the final formulation comprises approximately up to 67.62% SR PEG 400 |
| Propylene glycol | 9.78 |
| BHT | 0.10 |
| PEG 4000 | 17.50 |
| Pritelivir hemihydrate | 5.0 |

Photostability testing of the lead formulation 01v3 containing pritelivir hemihydrate to confirm the formulation prepared using this form of pritelivir was stable following exposure to light. Samples of filled borosilicate vials containing O1v3 were exposed to light according to ICH Guidelines Q1B and the pritelivir recovery and purity levels have been summarised in Tables 12 and 13, respectively.

Formulation was exposed to UV light under ICH conditions (1.2 million Lux hours and over 200 Watt hours per square meter).

The data illustrates that after exposure to UV light the pritelivir in formulation (O1v3) appeared stable due to little change in percentage recovery and purity of pritelivir from t=0.

TABLE 12

Mean percentage recovery of pritelivir hemihydrate (%) at t = 0 and following exposure to UV light according to ICH Guidelines Q1B mean (range n = 3)

| O1v3 | Mean percentage recovery of pritelivir hemihydrate (%) at t = 0 and following exposure to UV light. | |
|---|---|---|
| (5%) | T = 0 | Photostability |
| | 100.4 (98.02-103.75) | 104.24 (103.61-105.11) |

*In this case "T0: represents formulation prior to exposure to photostress conditions while, "pbhotostability" indicates samples after exposure to photostress conditions

TABLE 13

Mean purity levels of pritelivir hemihydrate (% a/a) at t = 0 and following exposure to UV light according to ICH Guidelines mean (range n = 3)

| O1v3 | Mean purity levels of pritelivir hemihydrate (% a/a) at t = 0 and following exposure to UV light. | |
|---|---|---|
| (5%) | T = 0 | Photostability |
| | 99.95 (99.95-99.95) | 100.00 (100.00-100.00) |

*In this case "T0: represents formulation prior to exposure to photostress conditions while, "pbhotostability" indicates samples after exposure to photostress conditions

SUMMARY OF SOME EMBODIMENTS

1. A N-[5-(amino-sulfonyl)-4-methyl-1,3-thiazol-2-yl]-N-methyl-2-[4-(2-pyridinyl)phenyl]acetamide free base hemihydrate having the molecular formula $C_{18}H_{18}N_4O_3S_2 \times 0.5H_2O$.
2. The N-[5-(amino-sulfonyl)-4-methyl-1,3-thiazol-2-yl]-N-methyl-2-[4-(2-pyridinyl)phenyl]acetamide free base hemihydrate according to embodiment 1 having a relative molecular mass of $M_r$ 411.50.
3. The N-[5-(amino-sulfonyl)-4-methyl-1,3-thiazol-2-yl]-N-methyl-2-[4-(2-pyridinyl)phenyl]acetamide free base hemihydrate according to any one of embodiments 1 and 2, which comprises XRPD peaks at 5.9, 11.7, 15.5 and 18.7 2theta.
4. The N-[5-(amino-sulfonyl)-4-methyl-1,3-thiazol-2-yl]-N-methyl-2-[4-(2-pyridinyl)phenyl]acetamide free base hemihydrate according to any one of embodiments 1 to 3, which has a melting point of 205° C. to 211° C.
5. The N-[5-(amino-sulfonyl)-4-methyl-1,3-thiazol-2-yl]-N-methyl-2-[4-(2-pyridinyl)phenyl]acetamide free base hemihydrate according to any one of embodiments 1 to 4 having a calculated pKa value of 4.53.
6. The N-[5-(amino-sulfonyl)-4-methyl-1,3-thiazol-2-yl]-N-methyl-2-[4-(2-pyridinyl)phenyl]acetamide free base hemihydrate according to any one of embodiments 1 to 5 having an octanol/water partition coefficient of 0.911±0.891 at 25° C.
7. The N-[5-(amino-sulfonyl)-4-methyl-1,3-thiazol-2-yl]-N-methyl-2-[4-(2-pyridinyl)phenyl]acetamide free base hemihydrate according any one of the embodiments 1 to 6 having a stability at a pH in the range of 4.5 to 7.0 of 90-100%.
8. A pharmaceutical composition comprising N-[5-(amino-sulfonyl)-4-methyl-1,3-thiazol-2-yl]-N-methyl-2-[4-(2-pyridinyl)phenyl]acetamide free base hemihydrate according to any one of the preceding embodiments, wherein said composition further comprises at least one pharmaceutically acceptable excipient.
9. A pharmaceutical composition obtainable by formulating N-[5-(amino-sulfonyl)-4-methyl-1,3-thiazol-2-yl]-N-methyl-2-[4-(2-pyridinyl)phenyl]acetamide free base hemihydrate as defined in any one of the preceding embodiments 1 to 7 with at least one pharmaceutically acceptable excipient.
10. The pharmaceutical composition according to any one of embodiments 8 and 9, further comprising an active ingredient selected from the group comprising anti-inflammatory agents, anti-viral agents, centrally and peripherally acting analgesics, anaesthetics.
11. The pharmaceutical composition according to any one of embodiments 8 to 10 further comprising a UV blocking agent.
12. A pharmaceutical composition as defined in embodiments 8 to 11, wherein said composition is selected from the group comprising topical formulations for patch administration, creams, ointments, salves, gels, skin lotions, wax formulations, lipsticks, tonics, mousses, foams, sprays, films, emulsions, pastes, solutions, oils, and lipogels, and patches.
13. The pharmaceutical composition as defined in any one of embodiments 8 to 12, wherein N-[5-(amino-sulfonyl)-4-methyl-1,3-thiazol-2-yl]-N-methyl-2-[4-(2-pyridinyl)phenyl]acetamide free base hemihydrate has a photostability in terms mean percentage recovery of about 95 to 107%, particularly about 103.61 to 105.11% as measured according to ICH guideline Q1B.
14. The pharmaceutical composition as defined in any one of embodiments 8 to 13, wherein the N-[5-(amino-sulfonyl)-4-methyl-1,3-thiazol-2-yl]-N-methyl-2-[4-(2-pyridinyl)phenyl]acetamide free base hemihydrate has a photostability according to ICH guideline Q1B in terms of a mean purity of about 95 to 105% area/area, advantageously in the range of 98 to 102% area/area.
15. The pharmaceutical composition as defined in any one of embodiments 8 to 14, wherein the N-[5-(amino-sulfonyl)-4-methyl-1,3-thiazol-2-yl]-N-methyl-2-[4-(2-pyridinyl)

phenyl]acetamide free base hemihydrate as measured by HPLC in a Franz diffusion cell with a solution of 2% w/v Brij 98 in PBS as receiver fluid has a percentage recovery of about 90 to 118% (92.24 to 114.49) at t=0, about 102 to 105% (103.16 to 103.71%) at t=24 at 2 to 8° C. and about 100 to 102 (101.47 to 101.70) at 37° C. at t=25 hours, about 102 to 108 (103.57 to 106.24) at t=48 hours at 2 to 8° C., and 104 to 118 (105.42-116.70) at t=48 hours at 37° C.; about 102 to 107 (103.78 to 105.69) at t=120 hours at 2 to 8° C., and about 84 to 98 (85.85-96.40) at t=120 hours at 37° C.

16. The pharmaceutical composition as defined in any one of embodiments 8 to 15, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 0.1 to about 10% w/w.

17. The pharmaceutical composition as defined in any one of embodiments 8 to 16, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 1.0 to about 7.5% w/w.

18. The pharmaceutical composition as defined in any one of embodiments 8 to 17, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 2.5 to about 6.0% w/w.

19. The pharmaceutical composition or topical pharmaceutical composition as defined in any one of embodiments 8 to 18, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 5.0% w/w.

20. The pharmaceutical composition as defined in any one of embodiments 8 to 19, wherein the N-[5-(amino-sulfonyl)-4-methyl-1,3-thiazol-2-yl]-N-methyl-2-[4-(2-pyridinyl)phenyl]acetamide free base hemihydrate is present in an amount of 5.0% w/w, wherein the pharmaceutical composition is an ointment.

21. The pharmaceutical composition as defined in any one of embodiments 8 to 20, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 1.0 to about 7.5% w/w, particularly about 5.0% w/w, wherein the pharmaceutical composition is an ointment, and wherein the ointment is administered 1 to 10 times a day, or 2 to 10 times a day, or 3 to 8 times a day, or 3 to 7 times a day, or 4 to 6 times a day, or 5 times a day.

22. The pharmaceutical composition as defined in any one of embodiments 8 to 21, wherein the N-[5-(amino-sulfonyl)-4-methyl-1,3-thiazol-2-yl]-N-methyl-2-[4-(2-pyridinyl)phenyl]acetamide free base hemihydrate is present in an amount of 1.0 to 7.5% w/w, particularly 5.0% w/w, wherein the pharmaceutical composition is an ointment, and wherein the ointment is administered 1 to 10 times a day, or 2 to 10 times a day, or 3 to 8 times a day, or 3 to 7 times a day, or 4 to 6 times a day, or 5 times a day, and wherein the ointment is administered over a period of 2 to 14 day, 3 to 10 days, 3 to 7 days, 4 to 5 days, or over 5 days, or over 4 days.

23. The pharmaceutical composition as defined in any one of embodiments 8 to 22, wherein the N-[5-(amino-sulfonyl)-4-methyl-1,3-thiazol-2-yl]-N-methyl-2-[4-(2-pyridinyl)phenyl]acetamide free base hemihydrate is present in an amount of 5.0% w/w, wherein the pharmaceutical composition is an ointment, and wherein the ointment is administered 5 times a day, and wherein the ointment is administered over a period of 4 days.

24. The pharmaceutical composition as defined in any one of embodiments 8 to 23, wherein the N-[5-(amino-sulfonyl)-4-methyl-1,3-thiazol-2-yl]-N-methyl-2-[4-(2-pyridinyl)phenyl]acetamide free base hemihydrate is present in an amount sufficient to reach a concentration of >10 nM in the epidermis and dermis of an individual subjected to a treatment with said composition.

25. N-[5-(amino-sulfonyl)-4-methyl-1,3-thiazol-2-yl]-N-methyl-2-[4-(2-pyridinyl)phenyl]acetamide free base hemihydrate according to any one of embodiments 1 to 7 for use as medicament.

26. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes virus infections.

27. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes virus infections, wherein said herpes viruses are selected from the order of simplex viruses.

28. N-[5-(amino-sulfonyl)-4-methyl-1,3-thiazol-2-yl]-N-methyl-2-[4-(2-pyridinyl)phenyl]acetamide free base hemihydrate as defined in any one of claims 1 to 7 for use in the treatment and/or prevention of herpes virus infections according to embodiment 27, wherein said simplex virus is selected from Herpes Simplex Virus 1 (HSV-1) and Herpes Simplex Virus 2 (HSV-2).

29. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in a oral pharmaceutical formulation in the treatment and/or prevention of a herpes virus infection in a subject in need thereof.

30. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in a topical pharmaceutical formulation in the treatment and/or prevention of a herpes virus infection in a subject in need thereof.

31. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in a topical pharmaceutical formulation in the treatment and/or preventive treatment of a subject in need thereof, wherein said subject has a herpes virus infection or is suspected to have a herpes virus infection 32. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in topical administration to a subject in need of a treatment and/or preventive treatment, wherein said topical administration is for skin application in general, facial application, and/or application to the mouth, the genitals, and/or the eyes.

33. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in systemic administration to a subject in need of a treatment and/or preventive treatment, wherein said subject is suspected to have a herpes virus infection or is a subject having a herpes virus infection.

34. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of recurrent herpes labialis.

35. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of recurrent herpes labialis selected from the group of patients showing signs of the prodromal stage of herpes labialis, patients having erythema, patients showing labial papules, patients having labial vesicles, patients with labial ulcers and/or soft crusts, patients having labial hard crusts, patients having residual labial erythema.

36. N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes genitalis.

37. The N-[5-(amino-sulfonyl)-4-methyl-1,3-thiazol-2-yl]-N-methyl-2-[4-(2-pyridinyl)phenyl]acetamide free base hemihydrate as defined in any one of claims 1 to 7 for use in the treatment and/or prevention of herpes keratitis 38. The N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes meningitis and/or encephalitis.

39. The N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes infections in the newborn.

40. The N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes infections in the immunocompetent and/or immunocompromised individuals.

41. The N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 for use in the treatment and/or prevention of herpes infections in immunocompromised individuals, wherein the immunocompromised individuals are selected from the group comprising recipients of an organ transplant, individuals having an infection by another virus or bacterium, particularly an infection with HIV and/or another herpes virus, and individuals infected with a herpes simplex virus that is resistant to at least one anti-viral active.

42. A method of treatment and/or prophylaxis of a herpes virus infection comprising administering N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7 to a subject in need thereof.

43. A method of manufacturing N-[5-(amino-sulfonyl)-4-methyl-1,3-thiazol-2-yl]-N-methyl-2-[4-(2-pyridinyl)phenyl]acetamide free base hemihydrate as defined in any one of embodiments 1 to 7, wherein said method comprises the following steps:
    a) Mixing 4-pyridine-2yl-phenyl)-acetic acid and amionothiazole sulfonic acid amide in N-Methylpyrorrolidone (NMP);
    b) Cooling the mixture obtained in step a);
    c) Adding N-Ethyl-N'-(3-dimethylaminopropyl)-carbodiimide hydrochloride (EDCxHCl) to said mixture obtained in step b);
    d) Stirring the solution obtained in step c) and addition to purified $H_2O$;
    e) Filtering the solution obtained in step d);
    f) Washing the product cake obtained in step e);
    g) Drying the product obtained in step f);
    h) Adding $H_2O$ to the solution obtained in step g);
    i) Stirring the suspension obtained in step h);
    j) Cooling the suspension obtained in step i);
    k) Stirring the suspension obtained in step j);
    l) Isolating the product by filtration of the suspension obtained in step k);
    m) Washing the product obtained in step l) with $H_2O$;
    n) Drying the product obtained in step m).

44. A pharmaceutical composition comprising a free base hemihydrate of N-[5-(amino-sulfonyl)-4-methyl-1,3-thiazol-2-yl]-N-methyl-2-[4-(2-pyridinyl)phenyl]acetamide obtainable in a method according to embodiment 43.

45. A pharmaceutical composition obtainable by formulation of a free base hemihydrate of N-[5-(amino-sulfonyl)-4-methyl-1,3-thiazol-2-yl]-N-methyl-2-[4-(2-pyridinyl)phenyl]acetamide obtainable in a method according to embodiment 43 with at least one pharmaceutical excipient.

46. Use of free base hemihydrate of N-[5-(amino-sulfonyl)-4-methyl-1,3-thiazol-2-yl]-N-methyl-2-[4-(2-pyridinyl)phenyl]acetamide obtainable in a method according to embodiment 43 as medicament.

The invention claimed is:

1. A N-[5-(amino-sulfonyl)-4-methyl-1,3-thiazol-2-yl]-N-methyl-2-[4-(2-pyridinyl)phenyl]acetamide free base hemihydrate having the molecular formula $C_{18}H_{18}N_4O_3S_2 \times 0.5H_2O$.

2. The N-[5-(amino-sulfonyl)-4-methyl-1,3-thiazol-2-yl]-N-methyl-2-[4-(2-pyridinyl)phenyl]acetamide free base hemihydrate according to claim 1, which comprises XRPD peaks at 5.9, 11.7, 15.5 and 18.7.

3. A pharmaceutical composition comprising N-[5-(amino-sulfonyl)-4-methyl-1,3-thiazol-2-yl]-N-methyl-2-[4-(2-pyridinyl)phenyl]acetamide free base hemihydrate according to claim 1, wherein said composition further comprises at least one pharmaceutically acceptable excipient.

4. A pharmaceutical composition obtained by formulating the N-[5-(amino-sulfonyl)-4-methyl-1,3-thiazol-2-yl]-N-methyl-2-[4-(2-pyridinyl)phenyl]acetamide free base hemihydrate as defined in claim 1 with at least one pharmaceutically acceptable excipient.

5. The pharmaceutical composition as defined in claim 3, wherein the N-[5-(amino-sulfonyl)-4-methyl-1,3-thiazol-2-yl]-N-methyl-2-[4-(2-pyridinyl)phenyl]acetamide free base hemihydrate is present in an amount of about 0.1 to about 10% w/w.

6. A medicament composition comprising N-[5-(amino-sulfonyl)-4-methyl-1,3-thiazol-2-yl]-N-methyl-2-[4-(2-pyridinyl)phenyl]acetamide free base hemihydrate according to claim 1.

7. A method for the treatment of herpes virus infection, which comprises administering to a subject in need thereof a composition comprising the N-[5-(amino-sulfonyl)-4-methyl-1,3-thiazol-2-yl]-N-methyl-2-[4-(2-pyridinyl)phenyl]acetamide free base hemihydrate as defined in claim 1.

8. The method of claim 7, wherein the herpes virus is selected from the order of simplex viruses.

9. A method according to claim 8, wherein the herpes virus infection is selected from recurrent herpes labialis, herpes genitalis, herpes keratitis, herpes meningitis, herpes encephalitis, or herpes infections in a newborn.

10. A method of manufacturing N-[5-(amino-sulfonyl)-4-methyl-1,3-thiazol-2-yl]-N-methyl-2-[4-(2-pyridinyl)phenyl]acetamide free base hemihydrate as defined in claim 1, wherein said method comprises the following steps:
   a) Mixing 4-pyridine-2yl-phenyl)-acetic acid and amionothiazole sulfonic acid amide in N-Methylpyrorrolidone (NMP);
   b) Cooling the mixture obtained in step a);
   c) Adding N-Ethyl-N'-(3-dimethylaminopropyl)-carbodiimide hydrochloride (EDC×HCl) to said mixture obtained in step b);
   d) Stirring the solution obtained in step c) and addition to purified $H_2O$;
   e) Filtering the solution obtained in step d);
   f) Washing the product cake obtained in step e);
   g) Drying the product obtained in step f);
   h) Adding $H_2O$ to the solution obtained in step g);
   i) Stirring the suspension obtained in step h);
   j) Cooling the suspension obtained in step i);
   k) Stirring the suspension obtained in step j);
   l) Isolating the product by filtration of the suspension obtained in step k);
   m) Washing the product obtained in step l) with $H_2O$;
   n) Drying the product obtained in step m).

11. A pharmaceutical composition comprising a free base hemihydrate of N-[5-(amino-sulfonyl)-4-methyl-1,3-thiazol-2-yl]-N-methyl-2-[4-(2-pyridinyl)phenyl]acetamide obtained by a method according to claim 10.

* * * * *